US012673171B2

(12) United States Patent
Thau et al.

(10) Patent No.: US 12,673,171 B2
(45) Date of Patent: Jul. 7, 2026

(54) DISPENSER WITH LID HANDLE

(71) Applicant: RPC Formatec GmbH, Mellrichstadt (DE)

(72) Inventors: Markus Thau, Mellrichstadt (DE); Johannes Krieger, Mellrichstadt (DE)

(73) Assignee: RPC Formatec GmbH, Mellrichstadt (DE)

( * ) Notice: Subject to any disclaimer, the term of this patent is extended or adjusted under 35 U.S.C. 154(b) by 973 days.

(21) Appl. No.: 17/629,494

(22) PCT Filed: Aug. 4, 2020

(86) PCT No.: PCT/EP2020/071908
§ 371 (c)(1),
(2) Date: Jan. 24, 2022

(87) PCT Pub. No.: WO2021/032469
PCT Pub. Date: Feb. 25, 2021

(65) Prior Publication Data
US 2022/0347407 A1 Nov. 3, 2022

(30) Foreign Application Priority Data
Aug. 19, 2019 (DE) .................... 20 2019 104 547.7

(51) Int. Cl.
*A61M 15/00* (2006.01)

(52) U.S. Cl.
CPC .... *A61M 15/0028* (2013.01); *A61M 15/0008* (2014.02); *A61M 15/0026* (2014.02); *A61M 2202/064* (2013.01)

(58) Field of Classification Search
CPC .......... A61M 15/0008; A61M 15/0026; A61M 15/0028; A61M 15/0043; B65D 2543/00833
See application file for complete search history.

(56) References Cited

U.S. PATENT DOCUMENTS

| | | | |
|---|---|---|---|
| 6,244,444 B1 * | 6/2001 | Jacobus | ............... B65D 25/205 |
| | | | 206/703 |
| 2006/0289515 A1 * | 12/2006 | Feuillas | ............... B65D 77/202 |
| | | | 219/729 |

(Continued)

FOREIGN PATENT DOCUMENTS

| | | | |
|---|---|---|---|
| DE | 10 2008 023 376 A1 | 11/2009 | |
| GB | 2299808 A * | 10/1996 | .......... B65D 43/169 |

(Continued)

OTHER PUBLICATIONS

International Search Report of PCT/EP2020/071908, mailed Nov. 19, 2020.

*Primary Examiner* — Kathryn E Ditmer
(74) *Attorney, Agent, or Firm* — Collard & Roe, P.C.

(57) ABSTRACT

A dispenser for powdery substances contained in a separate package that has a container part with removable container cover, wherein an aspirated air flow is further sucked predominantly through the container part after removal of the container cover, such that two air flows entering through slits in a lid that can be pivoted around a pivoting axis evacuate the container part from its two ends, and after merging enter a vortex chamber upstream from a mouthpiece. Outside air inlet openings for a third air flow are formed in a housing part covered by the lid in a radial extension to the pivoting axis.

3 Claims, 19 Drawing Sheets

(56)　　　　　　　References Cited

U.S. PATENT DOCUMENTS

2011/0061653  A1 *　3/2011　Von Schuckmann ........................
　　　　　　　　　　　　　　　　　　A61M 15/0028
　　　　　　　　　　　　　　　　　　128/203.15
2013/0074841  A1 *　3/2013　Von Schuckmann ........................
　　　　　　　　　　　　　　　　　　A61M 15/0025
　　　　　　　　　　　　　　　　　　128/203.15

FOREIGN PATENT DOCUMENTS

GB　　　　　　2408256  A  *　5/2005　................ A61J 1/03
PL　　　　　　149733  B1  *　3/1990
WO　　　　2009/138344  A1　11/2009
WO　　WO-2015110832  A1  *　7/2015　........ A61M 15/0003

* cited by examiner

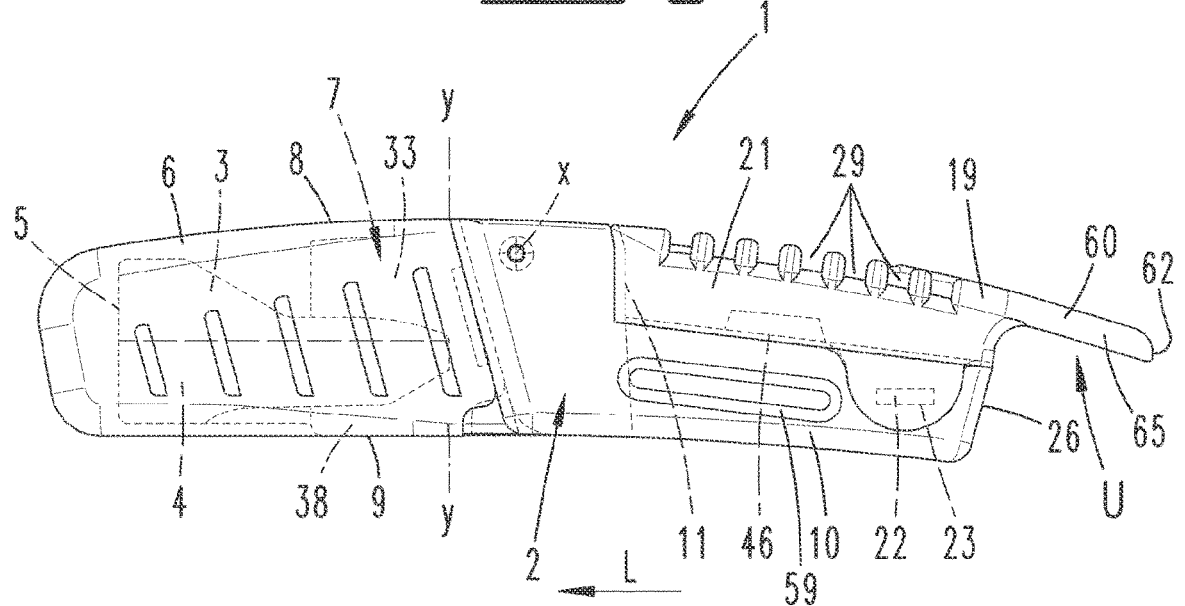

DISPENSER WITH LID HANDLE

CROSS REFERENCE TO RELATED APPLICATIONS

This application is the National Stage of PCT/EP2020/071908 filed on Aug. 4, 2020, which claims priority under 35 U.S.C. § 119 of German Application No. 20 2019 104 547.7 filed on Aug. 19, 2019, the disclosure of which is incorporated by reference. The international application under PCT article 21(2) was not published in English.

AREA OF TECHNOLOGY

The invention relates to a dispenser for powdery substances contained in a separate package, in particular substances contained in a blister package, wherein the package has a container part with removable container cover, wherein an aspirated air flow is further sucked predominantly through the container part after removal of the container cover from the container part, such that two air flows entering through slits in a lid that can be pivoted around a pivoting axis evacuate the container part from its two ends, and after merging get into a vortex chamber upstream from a mouthpiece, wherein outside air inlet openings for a third air flow are formed in a housing part covered by the lid in a radial extension to the pivoting axis.

PRIOR ART

For example, a dispenser of the kind in question is known from WO 2009/138344 A1.

Reference is further made to DE 10 2008 023 376 A1 with regard to prior art.

In the dispenser known from the last mentioned publication, the outside air inlet openings are formed in the lid itself, interrupted by riblike webs. The user accesses them during use. The lid is designed with contours that are nearly identical with the housing lying thereunder.

SUMMARY OF THE INVENTION

Proceeding from the described prior art, the invention deals with the task of giving a dispenser of the mentioned kind an advantageous design in terms of handling.

This object is achieved by a dispenser, wherein emphasis is placed on the fact that the lid is formed with a radial elongation relative to the pivoting axis in a partial area allocated to the outside air inlet openings for the third air flow over a width corresponding to one half or less of the width of the lid, wherein the elongation simultaneously forms an undergrip protrusion for opening the lid and freely protrudes over the adjacent, unelongated lid section, and the extent of the elongation in relation to the unelongated area corresponds to one fifth or more of the width of the lid.

As a result of this configuration, a dispenser of the kind in question is further improved in a manner beneficial to use. The provided elongation of the lid with an exposed design offers a convenient to grip handle for activating the lid, in particular for pivoting the lid around its pivoting axis. The exposed design of the elongation makes handling the dispenser intuitive, in particular for opening the lid.

In addition, the lid-side elongation overlaps the outside air inlet openings provided in the housing part for the third air flow in the closed lid position like a canopy. In a side view against the dispenser, with the geometric pivoting axis being represented as a point in said side view, the elongation proceeds from a root area of the elongation, in which the latter runs into the lid section extending over the entire width, and projects out over the lid section having the entire width.

The extent of the elongation, for example proceeding from the root area described above, and hence with respect to the adjacent, unelongated area, can here correspond to one fourth or more of the width, in particular of the largest width of the lid, preferably measures parallel to the alignment of the pivoting axis, further preferably to one fifth up to three fourths, for example, of the largest lid width.

The largest width of the elongation likewise preferably viewed parallel to the alignment of the pivoting axis, for example which according to one possible embodiment can form in the root area of the elongation, can further correspond to about half or less, for example up to one fourth, of the width, in particular of the largest width of the lid viewed in a parallel alignment to the pivoting axis.

As also preferred, the elongation can be designed as a single piece and/or in a materially uniform manner with the lid. In a preferred configuration of the lid as a plastic injection molded part, the elongation can further be formed simultaneously in this injection molding process for manufacturing the lid, if necessary in a two-component injection molding process, in which a second plastic component can be provided in particular in relation to the elongation. The elongation can here be provided with a second plastic component or be comprised of the latter, whether completely or even just partially, for example on the edge or surface or underside.

With respect to the disclosure, the areas or value ranges or multiple ranges indicated above and below also include all intermediate values, in particular in $1/10$ increments of the respective dimension, i.e., possibly also dimensionless. For example, the indication one half (0.5-fold) or less also includes the disclosure of 0.49 or less, the disclosure of one fourth (0.25-fold) or more also includes the disclosure of 0.26 or more, for example. This disclosure can serve to limit a mentioned range boundary from below and/or above, but alternatively or additionally to disclose one or several singular values out of a respectively indicated range.

BRIEF DESCRIPTION OF THE DRAWINGS

The invention is described below based on the attached drawings, with the latter only constituting an exemplary embodiment. The drawing shows:

FIG. 2 a side view of the dispenser according to arrow II on FIG. 1;

FIG. 9 a top view thereof;

FIG. 16 a longitudinal sectional view corresponding to FIG. 15, but relating to the dispenser standby position;

DESCRIPTION OF THE EMBODIMENTS

Figure 1G:
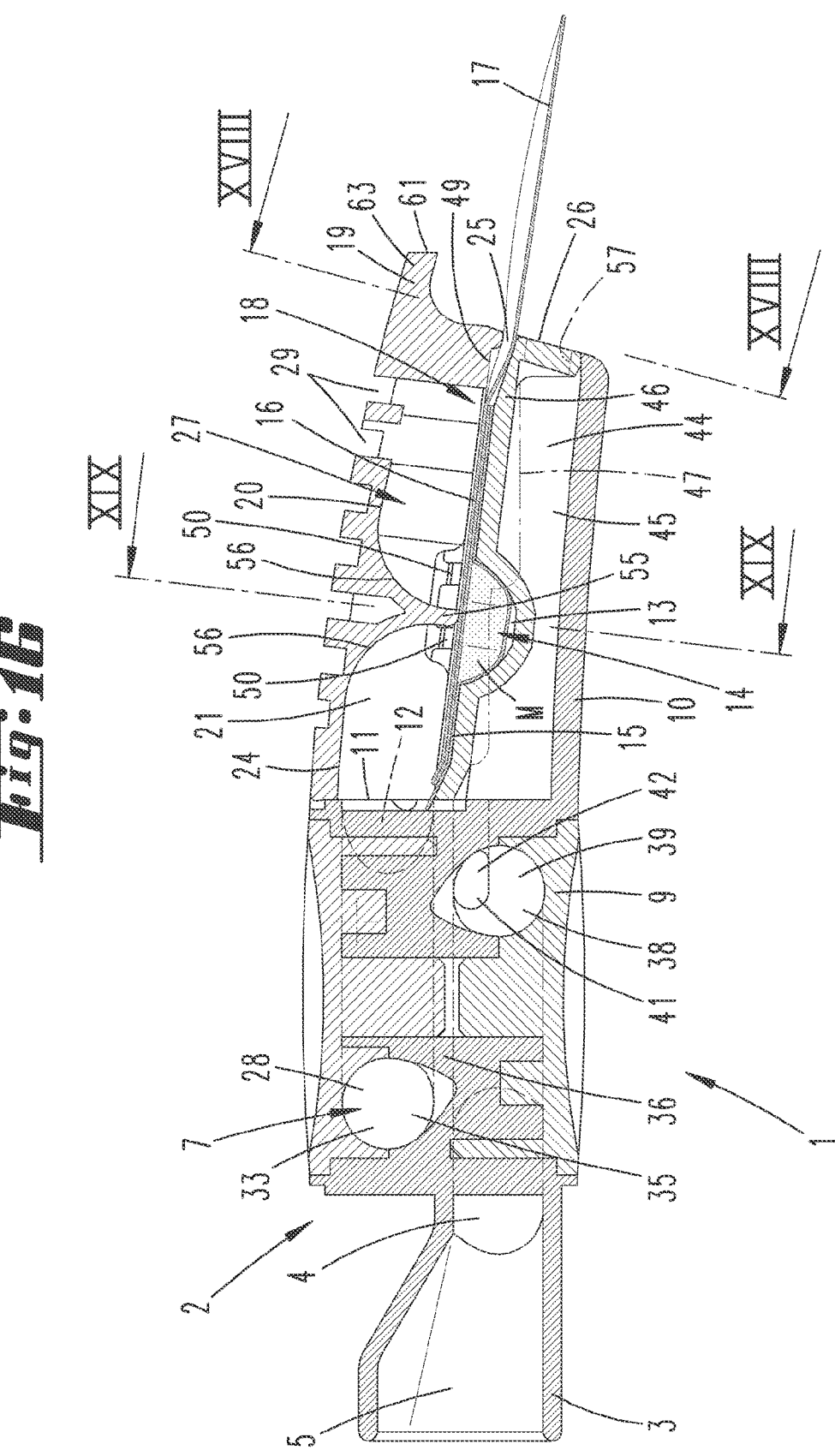
FIG. 1 a perspective view of the dispenser of the kind in question, relating to the nonuse position.
Figure 17:
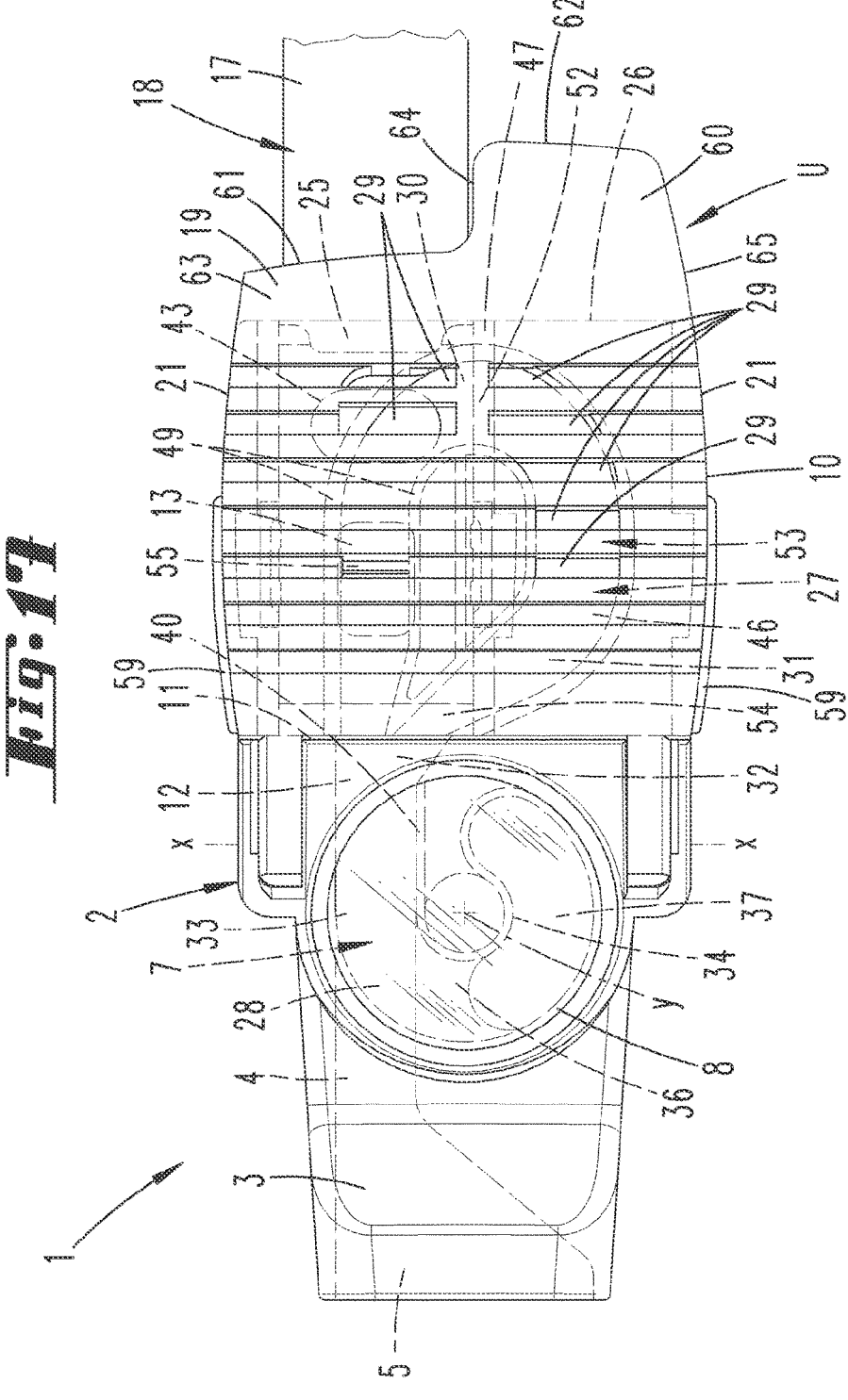
FIG. 17 a top view corresponding to FIG. 9, but relating to the position according to FIG. 16.
Figure 18:
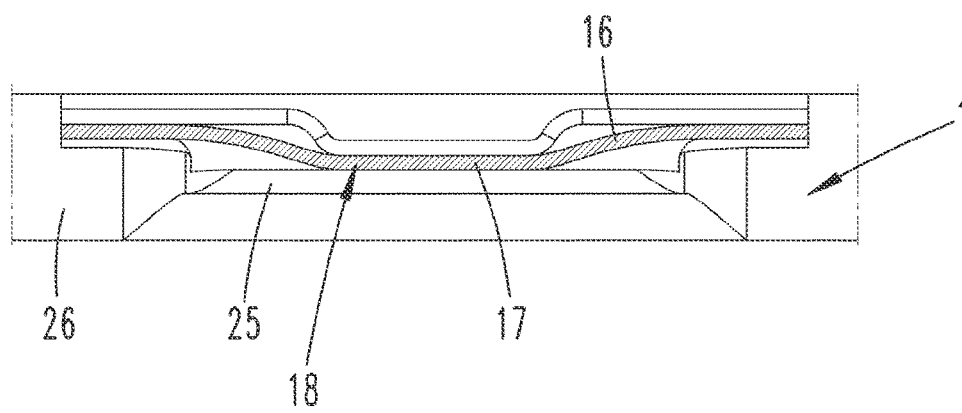
FIG. 18 the section according to line XVIII-XVIII on FIG. 16.
Figure 19:
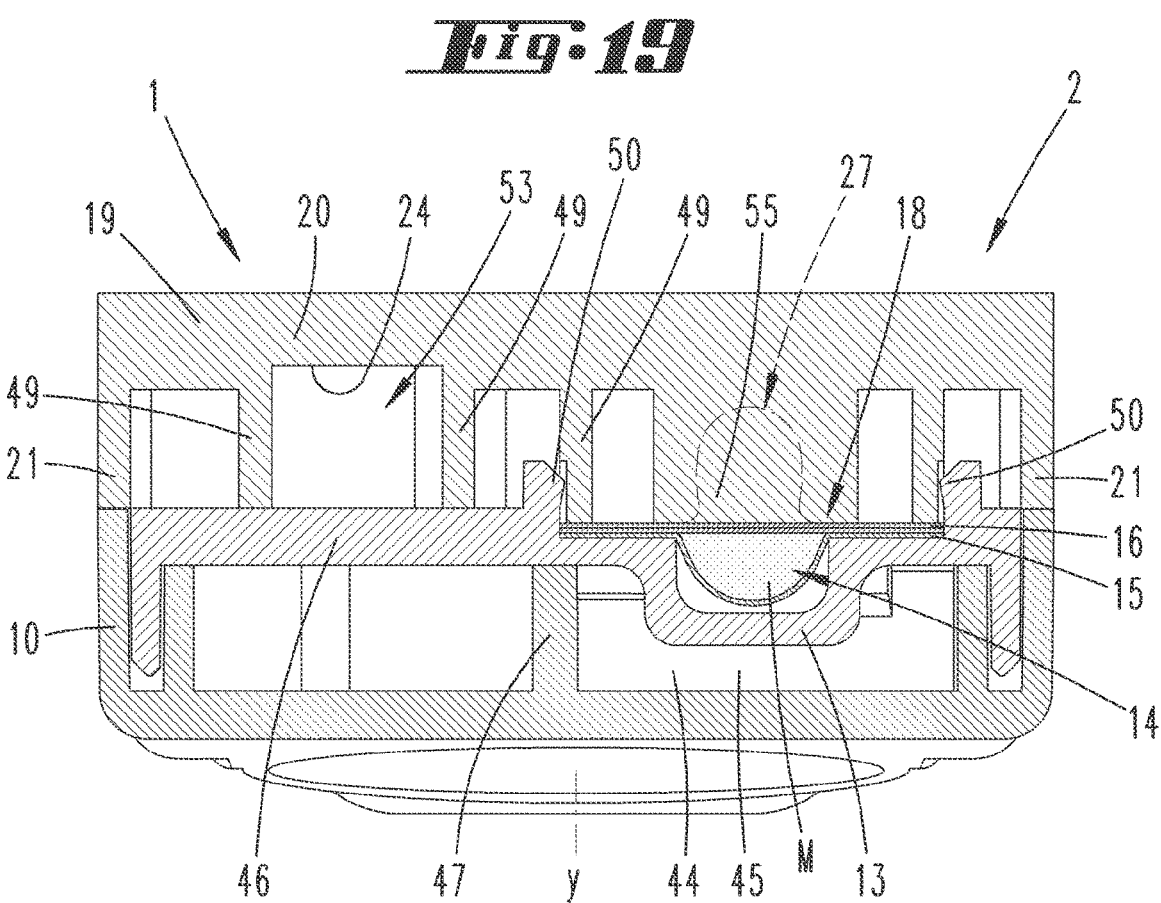
FIG. 19 the section according to line XIX-XIX on FIG. 16.
Figure 20:
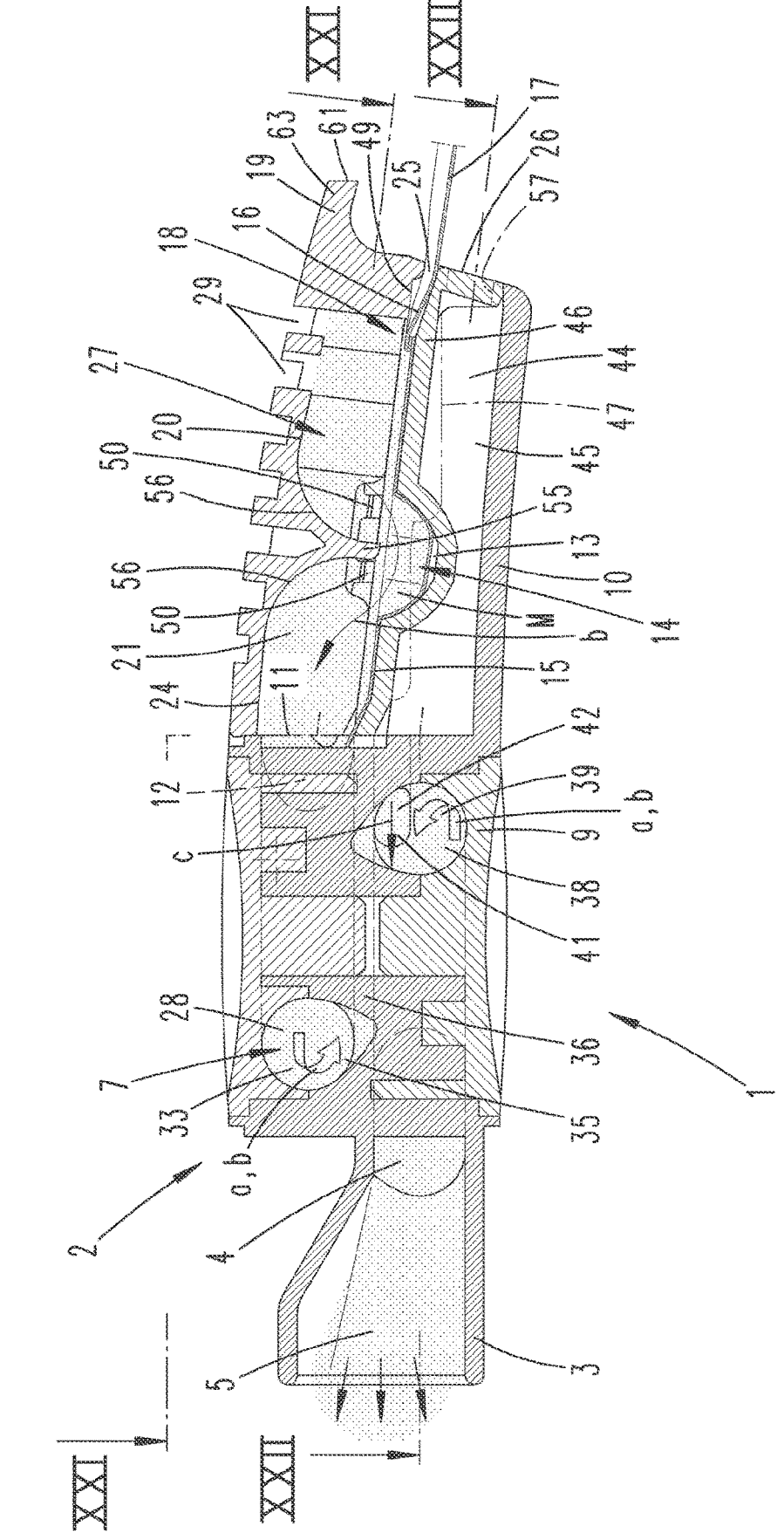
FIG. 20 a view corresponding to FIG. 16, but during an inhalation process.
Figure 21:
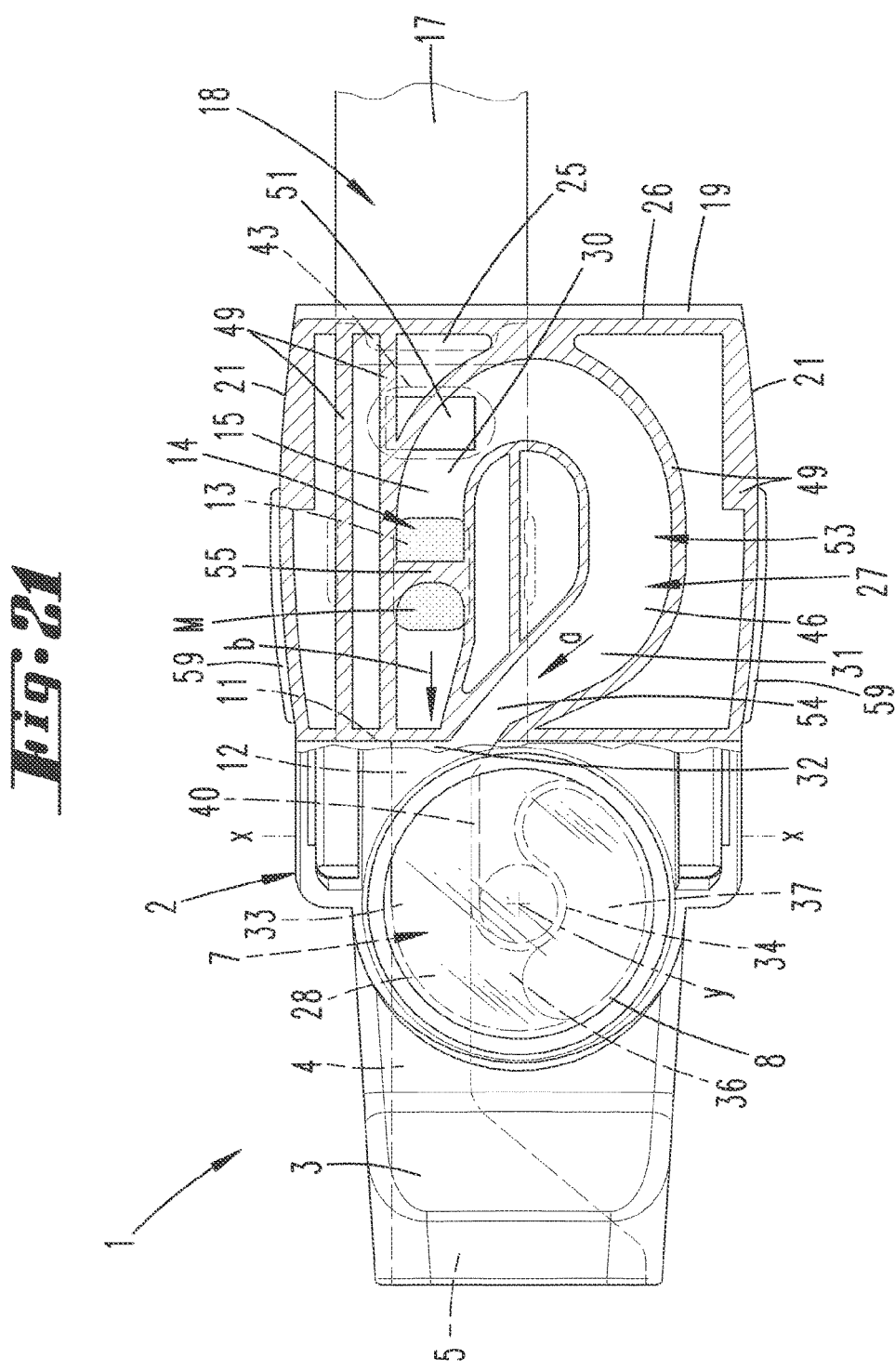
FIG. 21 the section according to cutting course XXI-XXI on FIG. 20.
Figure 22:
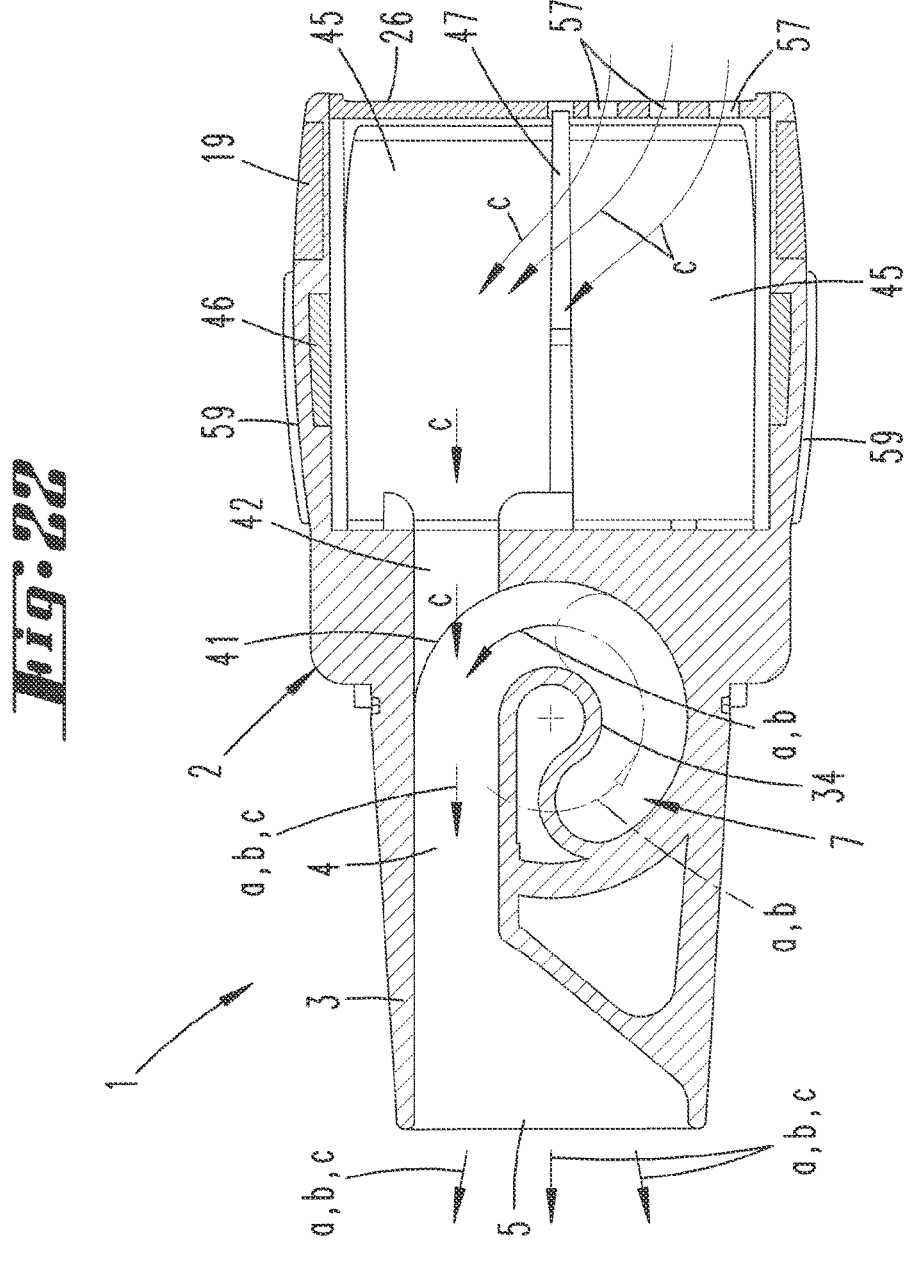
FIG. 22 the section according to cutting course XXII-XXII on FIG. 20.

Shown and described initially with reference to FIGS. 1 and 2 is a dispenser 1 in the form of an inhalator, which is realized as a convenient to carry pocket device. The latter can have an essentially elongated, rectangular housing 2, with a length-to-width ratio of about 2:1 to 2.5:1, and a height viewed perpendicular to the longitudinal extension that corresponds to about one fourth of the measure of longitudinal extension. The parts of the dispenser 1 are preferably realized as plastic injection molded parts.

A mouthpiece 3 protrudes from the housing 2 in an elongation of its direction of extension L. The transition from the housing 2 to the mouthpiece 3 can be tailored with respect to the width extension of the housing 2 given an overall one-piece design.

A suction channel 4 penetrates through the mouthpiece 3 in a longitudinal extension L, and ends in a suction mouth 5 on the output side.

When the dispenser 1 is not in use, the mouthpiece 3 according to the views on FIGS. 1 and 2 can preferably be covered by a closure cap 6. The latter essentially takes up the width of the housing 2, and is pluggable in the area of the tailored transition from the mouthpiece 3 to the housing 2.

Figure 12:
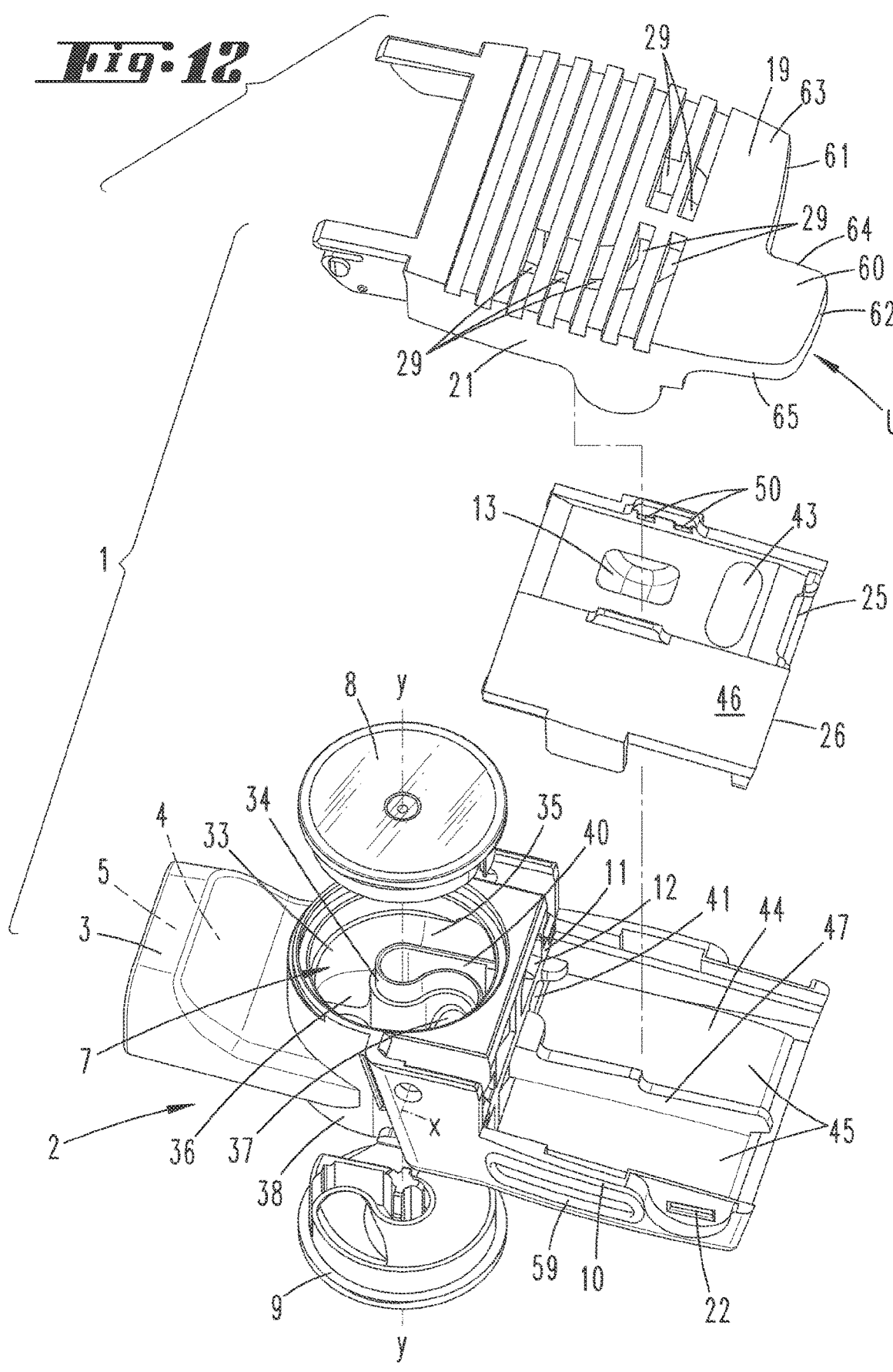
FIG. 12 an explosion perspective view of the dispenser.
Figure 13:
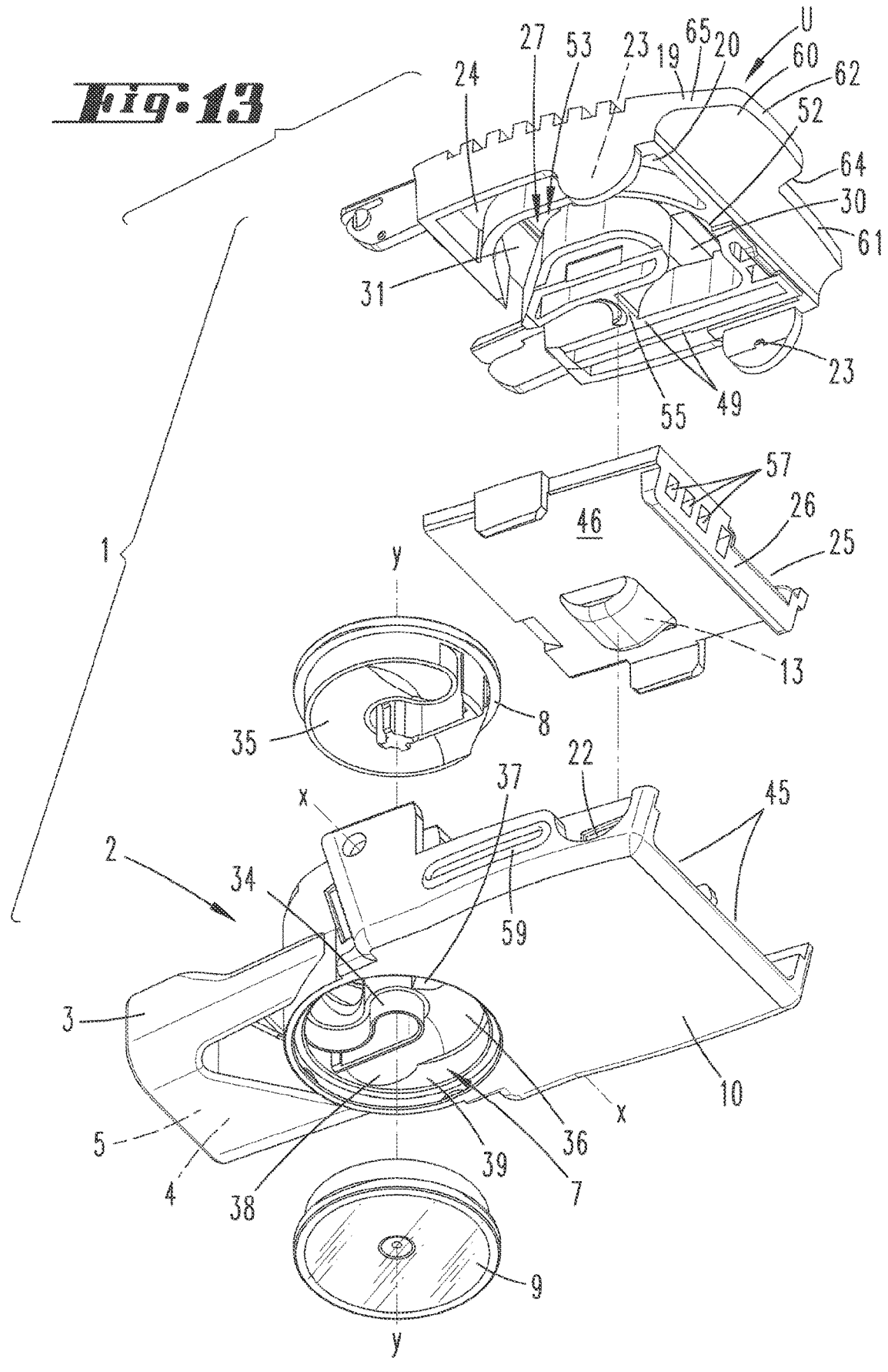
FIG. 13 another explosion perspective view of the dispenser.
Figure 15:
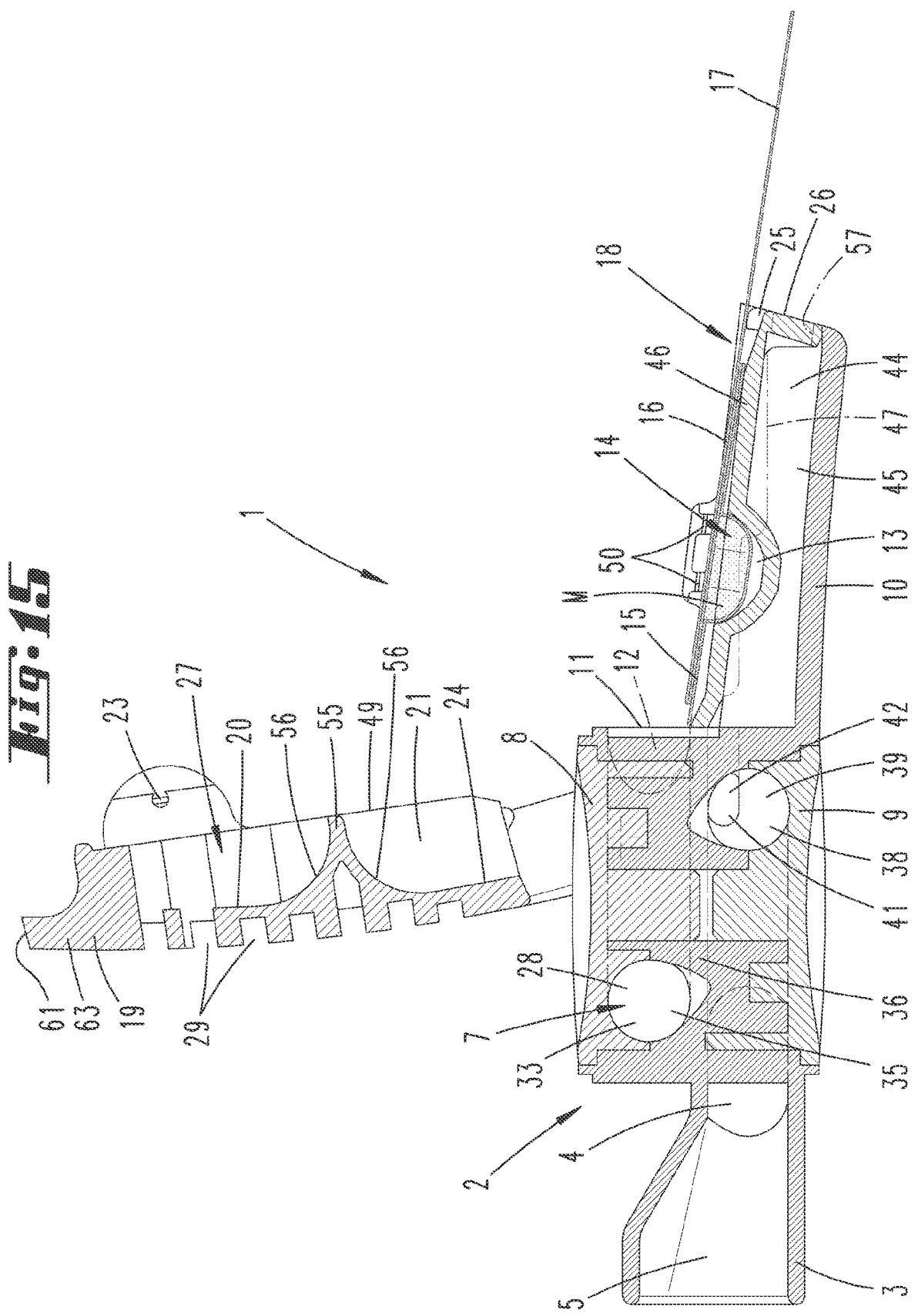
FIG. 15 the section according to line XV-XV on FIG. 9 with container part inserted.

Allocated to the transitional area from the housing 2 to the mouthpiece 3, a circular vortex chamber 7 with a vortex chamber axis y that runs essentially perpendicular to the suction channel 4 is formed in the housing 2 (compare FIG. 15). This vortex chamber 7 extends over two floors essentially over the entire height of the housing 2, wherein the chamber ceiling 8 as well as the chamber floor 9 are comprised of circular disk-shaped cover plates, which preferably are plugged onto the housing 2 (see FIGS. 12 and 13). The chamber ceiling 8 and chamber floor 9 can be transparent in design. An opaque configuration is also possible.

Figure 3:
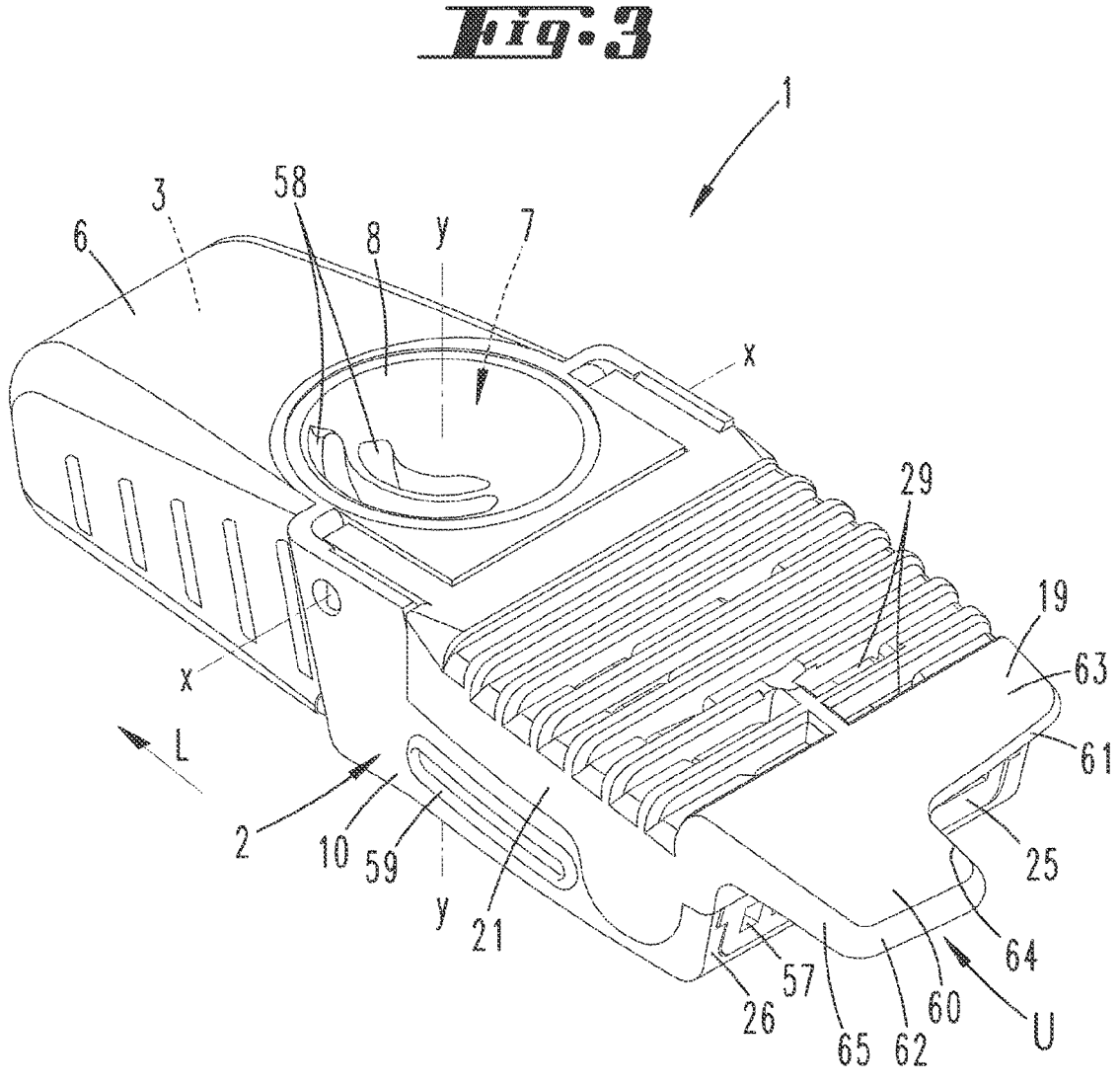
FIG. 3 the dispenser in another perspective view.
Figure 4:
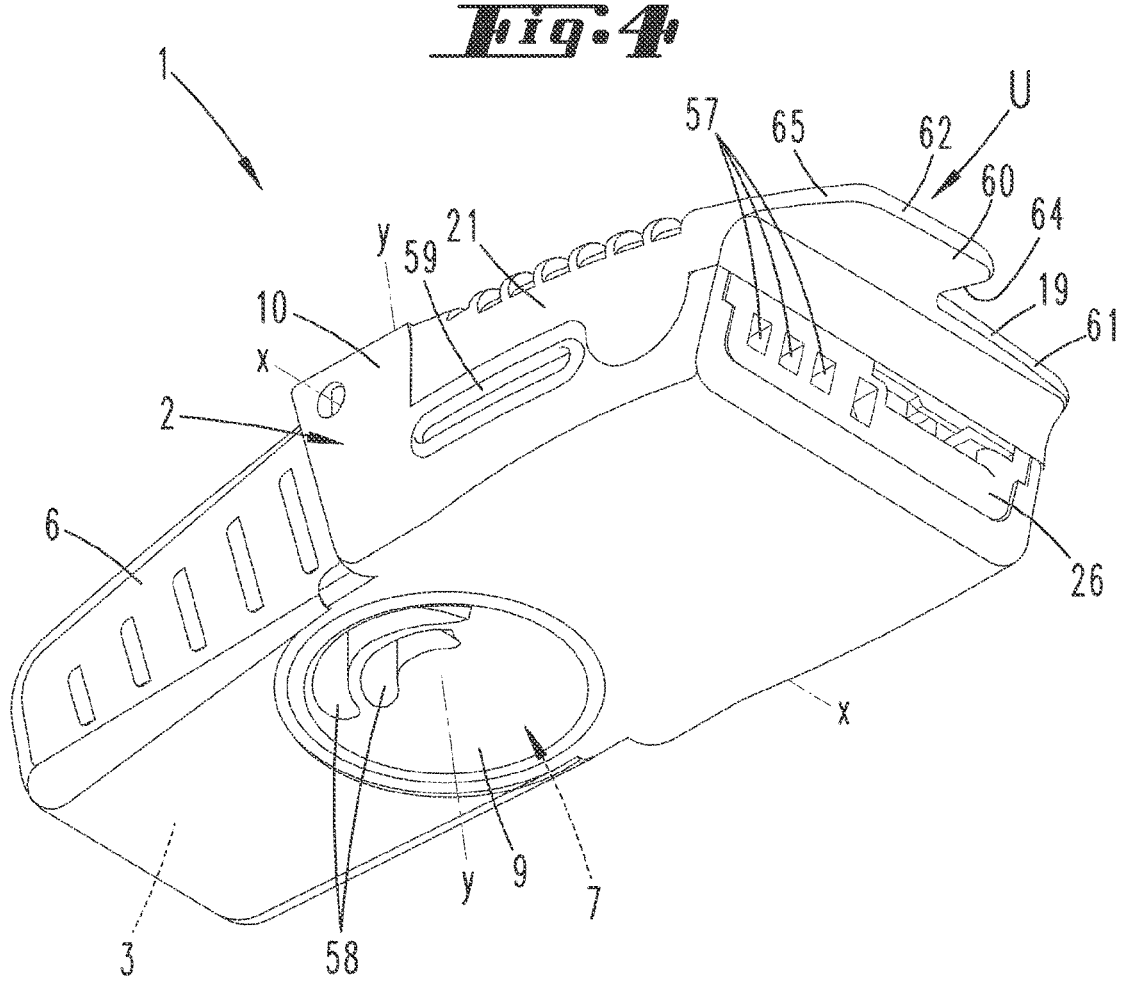
FIG. 4 another perspective view of the dispenser.

In addition, according to one possible embodiment, the chamber ceiling 8 and chamber ceiling [sic] 9, for example as evident from FIG. 3, can essentially be provided with slit-like recesses 58, for example that run essentially concentrically to the vortex chamber axis y. The latter can be axially outwardly open in design. By contrast, the latter are closed in the direction toward the covered vortex chamber 7.

For example, the recesses 58 can serve as an assembly aid. In addition, this embodiment produces comparatively thin chamber walls in the vortex chamber 7, and thus reduces the danger of sink marks.

Figure 10:
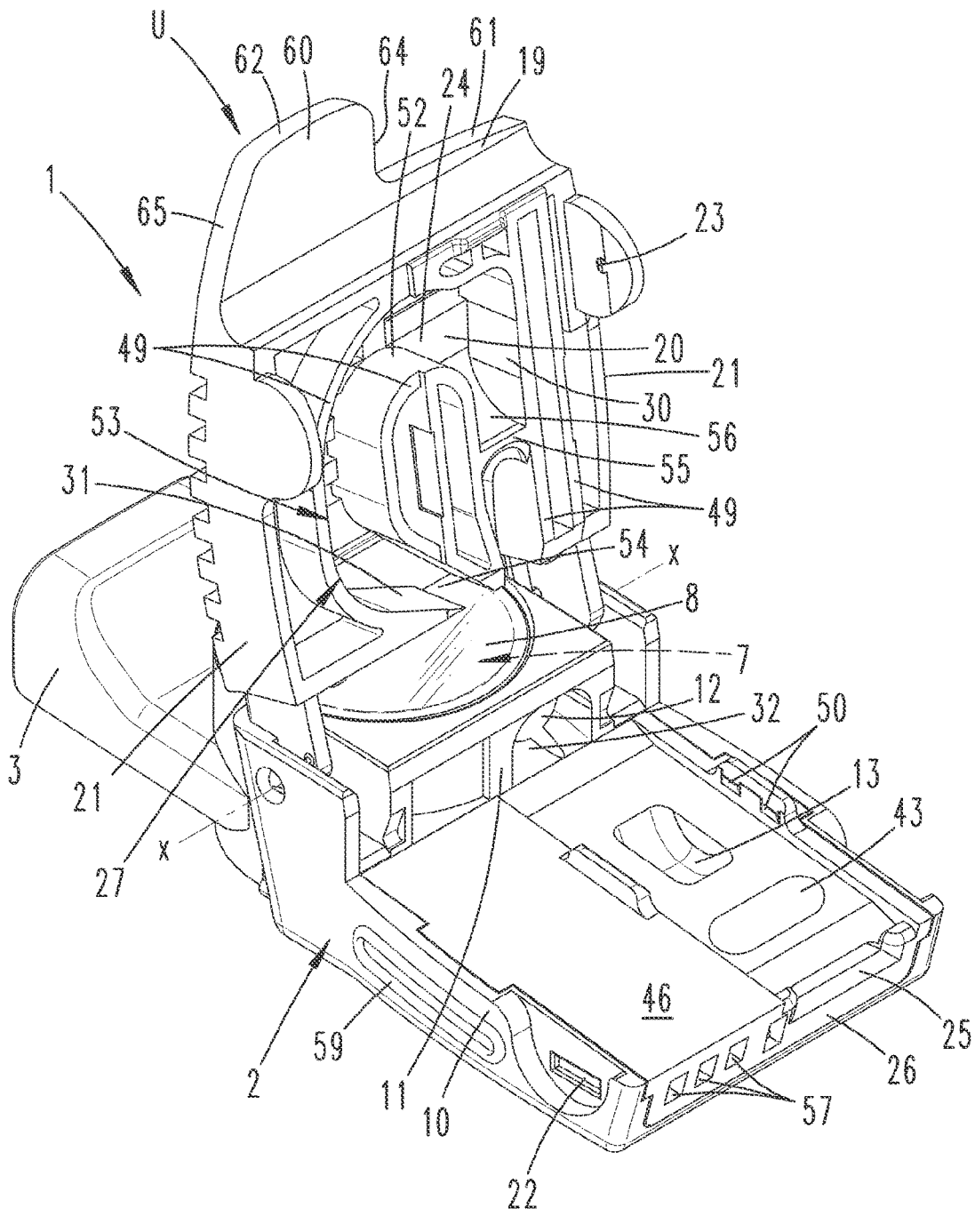
FIG. 10 a perspective view of the dispenser, relating to a standby position for equipping with a container part.

The housing part 10 facing away from the mouthpiece 3 and adjoining the vortex chamber 7 can be graduated in terms of height. The remaining surface plane of this housing part 10 offset vertically relative to the vortex chamber ceiling 8 extends in a central plane in relation to the vertical extension of the housing 2 (for example, compare FIGS. 10, 15 and 16). On the front side, i.e., facing the stepped plane of the housing part 10, an air channel 12 aligned essentially in the longitudinal extension of the housing 2 empties in the step 11 adjoining the vortex chamber 7 opposite the mouthpiece 3. It has a diameter that preferably corresponds to about 0.7 to 0.8 times the free step height. At the other end, this air channel 12 empties in the vortex chamber 7, in particular in the upper floor of the vortex chamber 7.

The area of the housing part 10 graduated in terms of height is initially open in design toward the top, facing away from a housing part floor, here essentially separated in the longitudinal extension by a vertical web 47 arranged centrally in relation to the width viewed transverse to the longitudinal extension, which correspondingly results in two areas that are at least approximately the same size on either side of the vertical web 47. These areas are covered by an intermediate floor 46, which correspondingly forms the stepped surface plane of the housing part 10. Essentially all around the edges, the intermediate floor 46 closes with the lower step edge, further below the mouth of the air channel 12 and with the edge boundary of the stepped area of the housing part 10, and is further preferably locked with the housing part 10 in an operationally undetachable manner.

A receptacle 13 that opens toward the flat surface is formed in the intermediate floor 46. It has an oblong layout, and is further formed at a distance to the air channel mouth in the step 11 in an axial elongation of the air channel 12. The contour and depth of the trough-like receptacle 13 is adjusted to the contour and height of a container part 14 to be received, correspondingly rounded in the longitudinal extension on the respective end side for receiving a capsule-like container part.

As evident from the additional illustrations in particular on FIGS. 14 to 21, the container part 14 is designed as a kind of blister package, wherein the container part 14 stocks a powdery substance M. For this purpose, the container part 14 is made out of a plastic material in a trough-like manner, wherein a flat support section 15 further adjoins the circumferential opening edge of the container part 14. As a whole, the container part 14 is designed as a depression out of the support section 15.

In the nonuse position, the substance M stocked in the container part 14 is sealed by an aluminum foil that covers the entire surface of the support section 15 and the container part 14, and comprises the container cover 16. This container cover 16 can be removed from the support section 15 to release the container part 14 or the substance M stocked therein, to which end the aluminum foil or the container cover 16 proceeds from a narrow area of the support section 15 aligned transverse to the longitudinal extension of the container part 14 and freely extends further in the opposite direction, thereby freely overlaying the area of the container cover 16 that seals the container part 14 and the support section 15. The free end of the container cover 16 protrudes freely over the front edge of the support section 15 that faces away from the turning area of the container cover 16 to form a fanlike puller handle 17.

The receptacle 13 formed in the intermediate floor 46 for the container part 14 is positioned in an area that is vertically more deeply offset relative to the intermediate floor surface. The vertical offset essentially corresponds to the material thickness of the blister 18 comprised of the container part 14, container cover 16 and support section 15 outside of the container part 14. In particular the length of the depression viewed in the longitudinal extension of the housing 2 is adjusted to the length of the support section 15 viewed in the longitudinal extension of the container part 14. The surface of the depression surrounding the receptacle 13 serves as a support for the support section 15 with the blister 18 inserted.

A lid 19 is allocated to the housing part 10. In the area of the step 11, it is hinged to the housing part 10 so that it can be folded around a pivoting axis x directed transverse to the longitudinal extension of the housing 2. The lid 19 has a cover 20. Side walls 21 running on either side in the longitudinal extension of the housing 2 are formed as one piece with the lid cover 20, and in the closed position of the lid flank the allocated side surfaces of the fixed housing part 10.

As also evident from the illustrations on FIGS. 3 to 8, for example, the lid 19 can be provided with an elongation 60 aligned in the longitudinal extension L of the dispenser 1. It can initially and essentially serve as an undergrip protrusion U for pivot actuating the lid 19.

Figure 5:
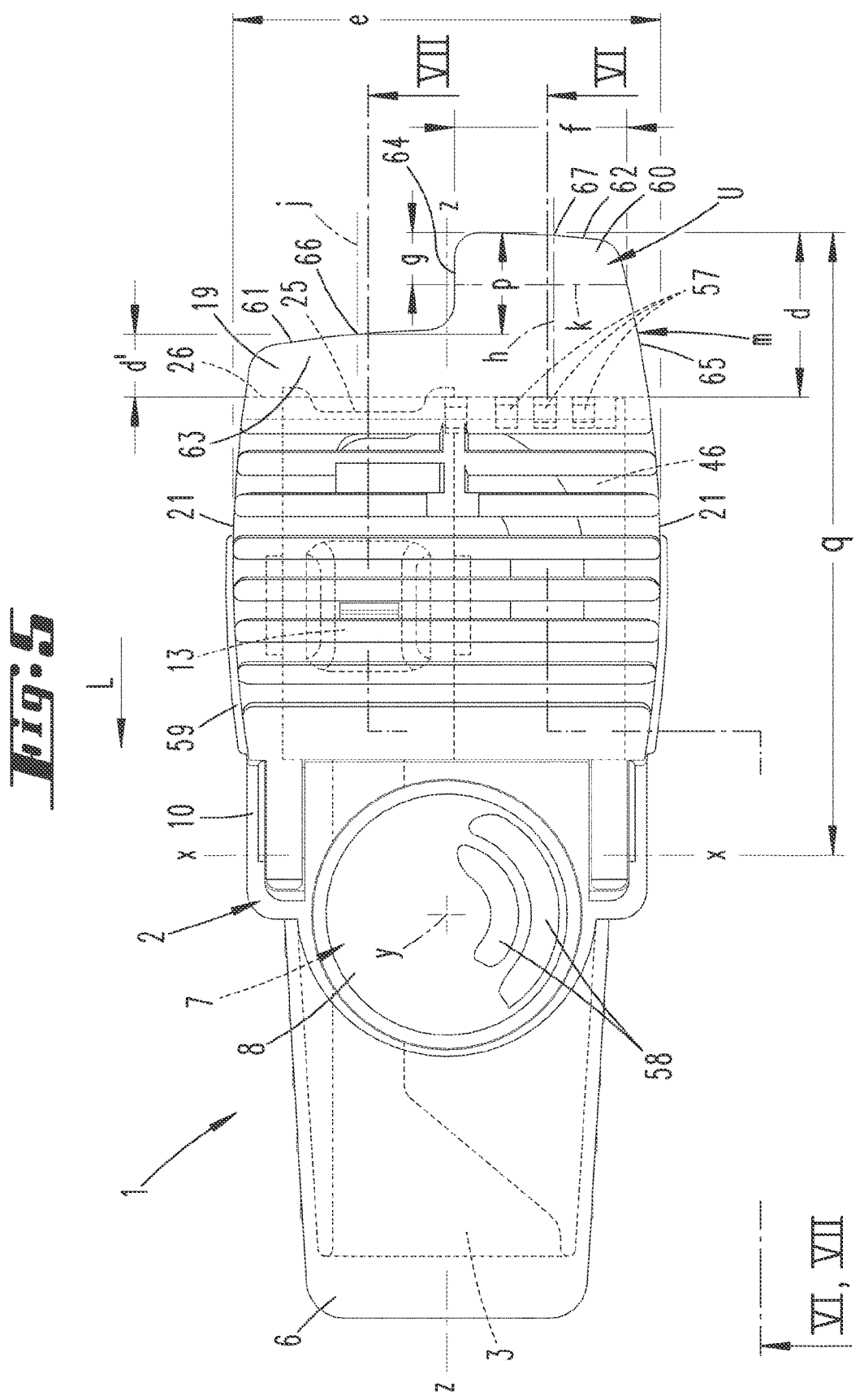
FIG. 5 a top view of the dispenser.

In relation to a top view according to FIG. 5, the elongation 60 can here extend over an edge surface 61 of the lid 19 facing away from the mouthpiece 3 to the side of a longitudinal central axis z of the dispenser 1. In a width extension, i.e., in a direction transverse to the longitudinal extension L, the elongation 60 preferably does not or does not significantly exceed the longitudinal central axis z, possibly touching the latter.

A width e of the lid 19 is removed on FIG. 5, as measured at the widest point of the lid 19 transverse to the longitudinal extension L or parallel to the pivoting axis x. This width e of the lid 19 can roughly correspond to the length q proceeding from the pivoting axis x up to the free front edge surface 62 of the elongation 60 measured in the longitudinal extension L, and further to about 1.1 to about 2 times this length q.

Along an auxiliary line k that penetrates through the elongation 60 while running transverse to the longitudinal extension L with reference to a top view according to FIG. 5, a width f of the elongation 60 arises that is preferably smaller than half the lid width e, i.e., corresponds to about 0.35 to 0.4 times the lid width e according to the exemplary embodiment depicted.

The auxiliary line k here runs with an offset dimension g to the area of the front edge surface 62 that is outermost viewed in the longitudinal extension L, with the offset dimension g corresponding to about 0.1 times the lid width e.

With respect to a rear wall 26 of the housing part 10, wherein outer air inlet openings 57 empty into this rear wall 26, as described in more detail further below, a length d of the elongation 60 viewed in the longitudinal extension L arises that can correspond to about 0.25 to 0.4 times, further for example to about one third of the width e and/or the lid length q. The length d is here measured along an additional auxiliary line h, with the auxiliary line h centrally penetrating through the auxiliary line k described above while aligned in the longitudinal extension L.

In a preferred configuration, the lid section 63 formed adjacent to the elongation 60 described above and having the edge surface 61 extends over the rear wall 26, similarly to the elongation 60, but only with a comparatively slight length dimension d', for example which can correspond to 0.25 to 0.5 times, further roughly to one third of the length dimension d of the elongation 60. The length dimension d' is here removed along an additional auxiliary line j (compare FIG. 5), with the auxiliary line j running centrally to the width extension of the lid section 63 in the area of the rear wall 26, proceeding from the longitudinal central axis z, in the longitudinal extension L.

As further evident from the top view on FIG. 5, an inner side edge surface 64 of the elongation 60 runs essentially in a parallel alignment to the longitudinal central axis z, wherein a respective radius can be provided in the transition to the edge surface 61 and to the front edge surface 62 of the elongation 60.

The outer side edge surface 65 preferably runs continuously into the facing outer wall surface of the lid 19, wherein the marginal edge resulting in the top view preferably runs along a circular arc with a radius m. The radius m can correspond to about 1.1 to 1.5 times the width e of the lid 19. With reference to the top view according to FIG. 5, this results in a tapering of the elongation 60 toward its free end.

Figure 6:
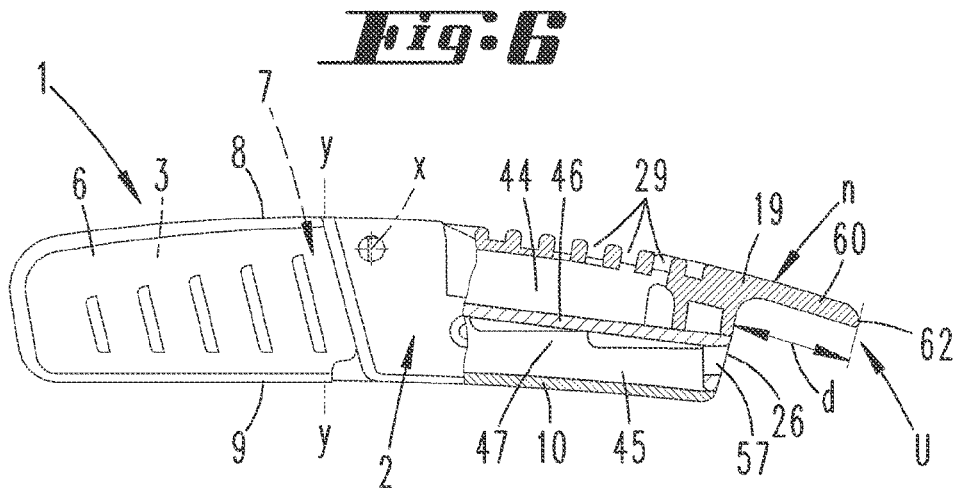
FIG. 6 the section according to line VI-VI on FIG. 5.
Figure 7:
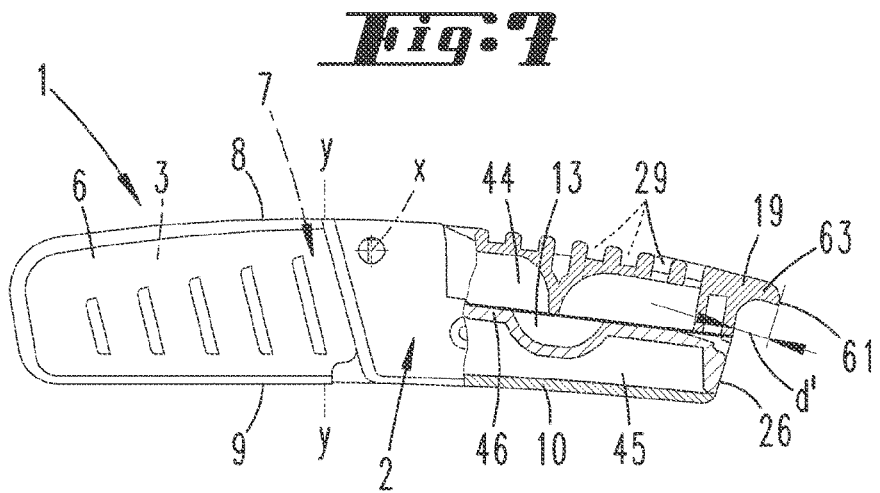
FIG. 7 the section according to lien VII-VII on FIG. 5.
Figure 8:
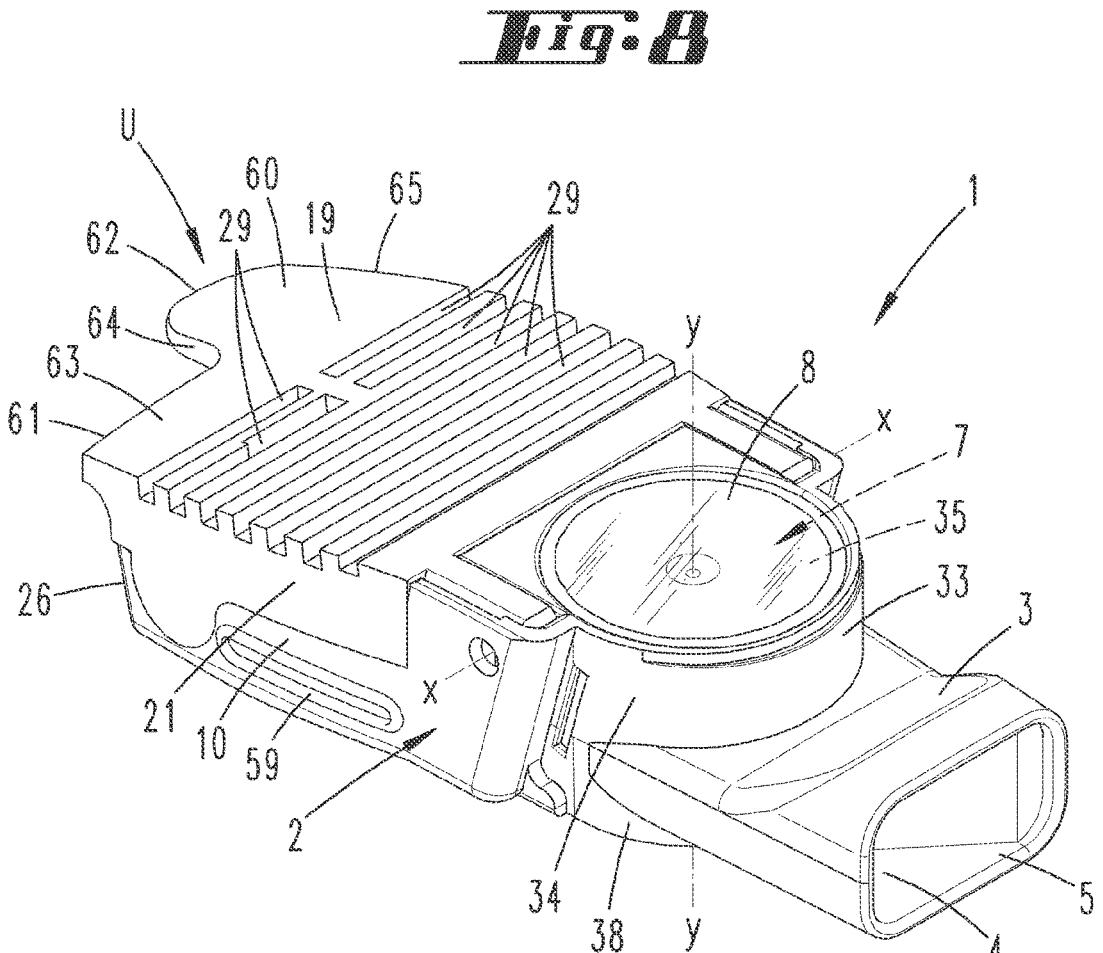
FIG. 8 another perspective view of the dispenser after removal of a suction mouth protective cap.
Figure 6:
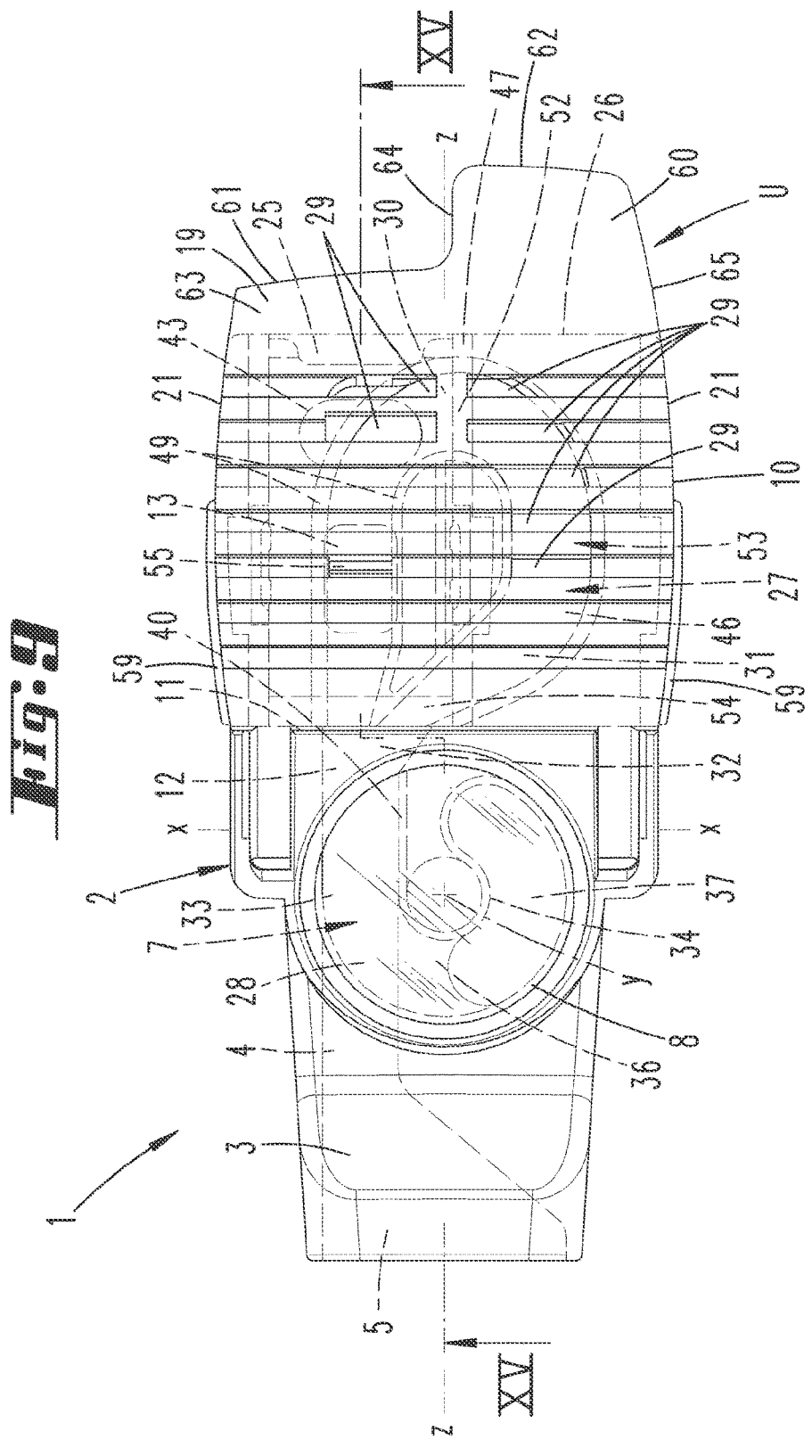

Visible in particular from the sectional views on FIGS. 6 and 7 are the different free lengths d and d' of the lid section 63 and the elongation 60. In particular these sections (lid section 63 and elongation 60) in the sectional views preferably run along a circular line with a radius n, wherein this radius n can preferably correspond to a multiple, for example 4 to 6 times, further preferably to about 5 times, the lid width e. The respective free end of the elongation 60 and the lid section 63 here tends to face beaklike in the direction of a floor plane of the dispenser 1 or the housing 2.

In particular on the surface side in a shared plane, the lid section 63 and the elongation 60 preferably run continuously into the remaining lid surface.

In particular with reference to the top view on FIG. 5, there arises an extent p to which the elongation 60 freely protrudes over the adjacent, unelongated lid section 63. This extent p results from a differential dimension, measured in the longitudinal extension L, between an intersection 66 between the centrally running auxiliary line j of the lid section 63 and the edge surface 61 as well as the intersection 67 between the auxiliary line h of the elongation 60 and its front edge surface 62. The dimension p can here correspond to one fifth or more of the width e of the lid 19, further for example to about 0.25 to 0.3 times the width e.

The elongation 60 of the lid 19 designed as described above offers the user an easy to handle, tabbed undergrip protrusion U, which allows the lid 19 to swivel open and shut.

The defined gripping area for opening the lid 19 that is hereby further preferably prescribed is additionally sufficiently spaced apart from the outside air inlet openings 57 in the rear wall 26.

The lid 19 is restrained in the lid closure position, for which purpose the side walls 21 of the lid 19 are provided with latching projections 23, which dive into housing part-side latching depressions 22. The latching bracket formed in this way can be easily surmounted by the user for opening the lid 19.

To make the dispenser 1 easy to handle, in particular during a lid actuation, riblike projecting formations 59 can be provided on the wall exterior of the housing part side walls, where the latching depressions 22 described above can also be formed, and make it possible to get an easy and reliable grip.

In the lid closure position, the ceiling underside 24 rests on the facing upper side of the intermediate floor 47 over vertical webs 49 integrally molded on the lower cover side, meaning preferably on the plan area that accommodates the receptacle 13 and surrounds the depression. With the blister 18 placed in the intermediate floor-side receptacle 13 and the accompanying compensation of the vertical offset in the intermediate floor 46, the lower cover side 24 or the vertical webs 49 provided on the lower cover side preferably lies on the blister 18, in particular on the container cover 16 that forms the puller handle 17 in the free end area. Accordingly, the inserted blister 18 is captured in the lid closure position by the roughly positive locking of the container part 14 in the receptacle 13 on the one hand, and on the top and bottom side by the lid cover 20 and the allocated surface of the intermediate floor-side depression on the other, wherein a lateral support of the blister 18 via the support section 15 is provided by the step 11 on the one hand, and by the edge boundary of the depression on the other.

In addition, the lid 19 with the vertical webs 49 provided on the lower lid side is also supported on the adjacent plan area of the intermediate floor 46 that is raised in relation to the depression accommodating the blister 18, wherein the vertical webs 49 of the lid 19 simultaneously at least partially border flow paths.

In the longitudinal extension of the depression accommodating the blister 18 in the intermediate floor 46, latching noses 50 are formed on either edge side of the depression, which in the container part allocation position overlap the support section 15, and in the nonuse position simultaneously also overlap the container cover 16, so that a blister 18 inserted with the lid 19 open is captured in the allocation position by the overlap of the latching noses 50. Due to the thin-walled and possibly elastic configuration in particular of the blister part-side support section 15, the latching noses 50 can be surmounted both during insertion of the blister 18 and during removal.

In addition, a mark 43 is applied on the surface side of the intermediate floor-side depression on the removal side of the receptacle 13, in particular in the form of a color mark. In the allocation position of the blister 18, this mark 43 vertically covers a windowlike cutout 51 in the support section 15, with this windowlike cutout 51 being exposed while removing the container cover 16 in preparation for inhalation.

The blister 18 must be placed in the dispenser 1 in such a way that the envelope edge of the container cover 16 is arranged facing the air channel 12 while aligned parallel to the pivoting axis x, and further that the freely sprawling puller handle 17 protrudes out of the housing 2 in the opposite direction over the depression boundary, while penetrating through a slit-like removal opening 25 correspondingly left between the intermediate floor 46 and the lid 19 pivoted into the closure position. The latter is adjusted in its width viewed transverse to the longitudinal extension of the housing 2 to the width of the container cover 16. The vertical height of the removal opening 25 essentially corresponds to the material thickness of the container cover 16.

An off-center arrangement of the receptacle 13 provided in the longitudinal extension of the dispenser 1 or the depression in the intermediate floor 46 ensures that the blister 18 to be inserted is correctly aligned in the dispenser 1. The blister 18 correspondingly has varying leg lengths of the support section 15 adjusted to the off-center arrangement of the receptacle 13 in the longitudinal extension, so that an insertion of the blister 18 in exclusively the predetermined alignment can be achieved.

In the lid closure position, the vertical webs 49 protruding on the lower lid side together with the facing surface of the intermediate floor 46 form an air flow channel 27, which with reference to a vertical projection on the intermediate floor 46 is guided like a kind of arced path. As a container channel section 30, the air flow channel 27 initially leads to the end of the intermediate floor-side receptacle 13 or the container part 14 accommodated in the receptacle 13 that is more remote in relation to the housing-side air channel 12. Proceeding from this end, the air flow channel 27 extends to a channel section that runs at least approximately parallel to the longitudinal alignment of the receptacle 13 while forming a 180° curvature radius 52, and that further transitions into a direct channel section 31 while enclosing the receptacle 13 on one side.

In an essentially axial elongation of the housing-side air channel 12, the air flow channel 27 is further formed at the other end of the receptacle 13 for a direct flow connection to the housing-side air channel 12 in the lid closure position. Together with the section of the air flow channel 27 allocated to the air channel 12, the direct channel section 31 empties into a unification section 32, which in the exemplary embodiment shown is formed in the area of the opening of the housing-side air channel 12 facing the air flow channel 27.

The arced path channel 53 that is formed in particular out of the container channel section 30 and the direct channel section 31 tapers in the direction toward the unification section 32 in terms of its free-flowing cross sectional surface in relation to the average cross sectional surface of the air flow channel 27, further preferably by about 40% of the average cross sectional surface. This tapered, nozzle-like end section of the direct channel section 31 is labeled with reference number 54.

A rib 55 is further molded onto the lower lid side, overlapping the receptacle 13 or the container part 14 placed in the receptacle 13. It extends transversely directed between two vertical webs 49 that border the section of the air flow channel 27 overlapping the receptacle 13, and viewed in the lid closure position here has a height selected in such a way that the free front edge of the rib 55 that protrudes downward in the inhalation standby position protrudes into the gap above the opened container part 14 that is exposed after removing the container cover 16.

Figure 11:
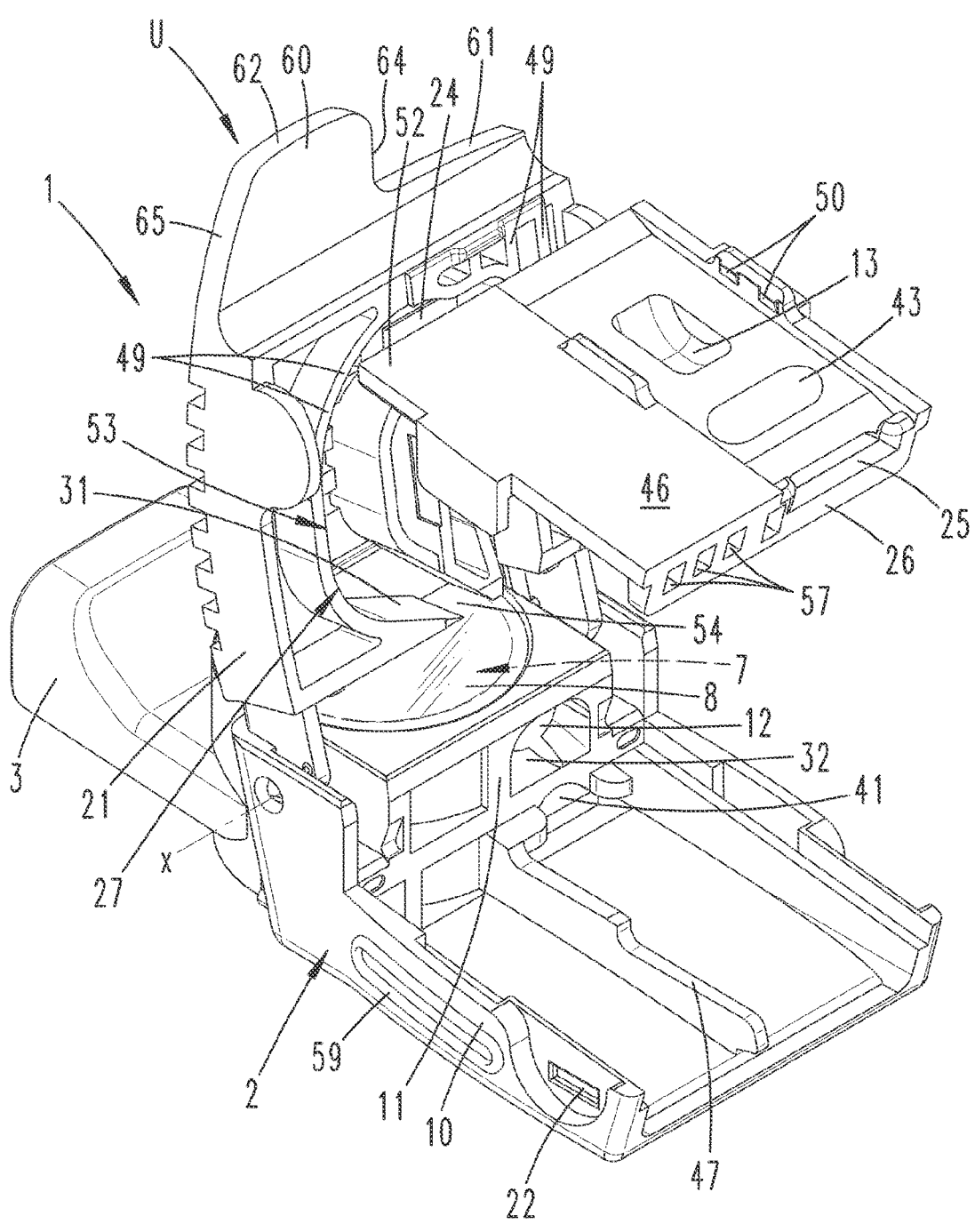
FIG. 11 another perspective view of the dispenser in the equipping standby position, with an intermediate floor arranged in an explosion perspective.

The rib 55 provides a deflection of the air flow channel 27 in the direction toward the receptacle 13 or toward the container part 14 located in the receptacle 13, as well as a deflection out of the latter. To achieve at least a low-loss deflection, the rib 55 is equipped on either side with hollow, concave side surfaces 56 in relation to a vertical section according to FIG. 11. These are provided with a radius preferably adjusted to the cross sectional radius of the air flow channel 27, wherein the free end area of the rib 55 facing downwardly in the direction toward the receptacle further has a width viewed in the direction of flow that corresponds to about 0.1 to 0.3 times, preferably to about 0.2 times, the length of the receptacle 13 viewed in the same direction.

In relation to a longitudinal extension of the receptacle 13 or the container part 14, the rib 55 is further aligned centrally and transversely to the longitudinal extension.

Figure 14:
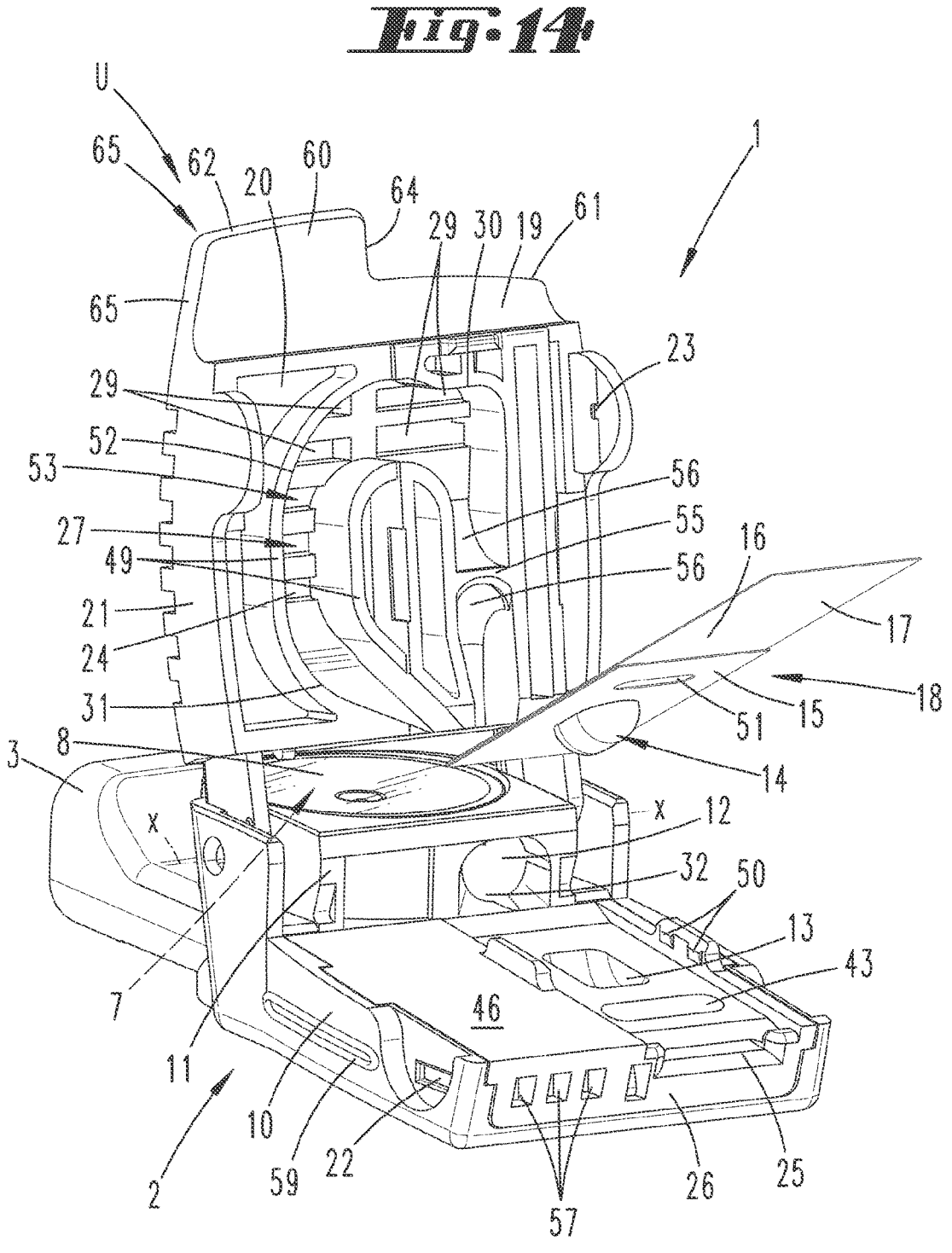
FIG. 14 another perspective view of the dispenser in the equipping standby position while being equipped with a container part.

After removal of the container cover 16 according to FIG. 14, the air flow channel 27 is correspondingly double-S guided due to the arrangement and configuration of the rib 55 described above, while also passing through the container part 14.

Overlapping the arc path channel 53, further in particular overlapping the curvature area 52, air inlet slits 29 are further provided in the lid cover 20, which preferably are open toward the top in the lid closure position, and further also open up while preferably passing through the side of the allocated side wall 21. This yields an inlet grid-like cover of in particular the curvature area 52.

At the other end, the housing-side air channel 12 that opens toward the housing part 10 empties into a deflection section 28 of the vortex chamber 7, further into an upper floor 33 of the vortex chamber 7, with this upper floor 33 essentially extending above the separation plane between the intermediate floor 46 and lid 19.

The upper floor 33 of the vortex chamber 7 is essentially annular in design, to which end a ring wall 34 extending over the entire height of the upper floor 33 is centrally provided. Proceeding from the air channel inlet, the annular channel 35 of the upper floor 33 extends roughly at an angle of 270° (counterclockwise in relation to the view on FIG. 4) before the annular space 35 passes through a through hole 37 that opens the floor bottom 36 and transitions into an annular channel 39 likewise formed in a floor 38 arranged thereunder. The latter is also bordered radially inward by the annular wall 34 that runs through essentially over the entire vertical height of the vortex chamber 7.

A separating wall 40 that closes the annular space in the circulating direction to the inlet of the air channel 12 is drawn immediately following the floor-side through hole 37 in the direction of flow in the area of the upper floor 33, and proceeds radially from the allocated annular wall section.

The annular channel 39 of the lower floor 38 extends proceeding from the 90° curvature area of the upper annular channel 35 over about 270° up to the connection to the suction channel 4 of the mouthpiece 3.

The through hole 37 that connects the floors or the annular channels 35 and 39 extends over an angular range of about 180°, which viewed in the direction of flow takes up the angular range of 90° to 270° of the upper annular channel 35 and the angular range of 270° to 90° of the lower annular channel 39. Correspondingly, a transition of the two annular channels over a range of about 180° is given.

In this way, the air is essentially helically guided in the vortex chamber 7, with the air aspirated through the vortex chamber circulating by 360° in all, further while passing through two planes arranged one below the other.

In the annular space 39 of the lower floor 38 of the vortex chamber 7, an outside air opening 41 empties into the upper floor 33 while vertically overlapping the mouth of the air channel 12, and its outside air channel 42 passes through the housing 2 in such a way that the outside air opening 41 opens tangentially toward the annular space 39. At the other end, the outside air channel 42 extends in the longitudinal extension of the housing 2 under the step-side opening of the air channel 12 and empties into the intermediate space 44 left between the intermediate floor 46 and the housing floor. The latter forms a secondary air channel 45, which is formed on the alternate side of the intermediate floor-side vertical web 47. The area of the intermediate space 44 formed below the receptacle 13 is closed off on the rear side of the housing by a vertically running rear wall 26 of the intermediate floor 46. In this end section allocated to the rear wall 26, the vertical web 47 that essentially divides the intermediate space 44 in the longitudinal extension is reduced in height, so as to establish a flow connection between the intermediate floor areas formed one next to the other, wherein outside air inlet openings 57 are allocated in the rear wall 26, allocated to the intermediate space area formed below the arced path channel 53. Accordingly, these outside air inlet openings 57 in the operational inhalation position are adjacent to the container cover 16 that protrudes out of the housing 2 on the rear wall side.

In order to inhale a substance M, a blister 18 is initially inserted after the lid 19 has been pivoted into the open position according to FIG. 9, such that the container part 14 is accommodated in the receptacle 13, with the blister-side support section 15 being supported on the allocated, recessed surface of the intermediate floor 46. The additionally provided latching noses 50 here overlap the support section 15, and preferably also the container cover 6 lying in the closure position, which is further present in two layers in particular in the area of the latching noses 50 owing to the envelope side guidance in the end area of the blister 18. The freely protruding puller handle 17 projects freely over the housing end for operational purposes.

After the lid 19 has been closed, the blister 18 is secured in the housing 2. The blister 18, in particular the puller handle 17, here extends to the side of the elongation 60, in particular allocated to the unelongated lid section 63. Accordingly, the elongation 60 and puller handle 17 extend arranged one next to the other. The puller handle 17 is exposed for handling in the free area of the lid 19 flanked by the elongation 60 (see FIG. 17).

After this, the container part 14 is opened by rolling off the container cover 16, to which end the puller handle 17 protruding through the removal opening 25 is pulled in the removal direction r. This removal process is visible due to the transparent design of the lid 19, in particular a transparent design of the section of the lid 19 that covers the displacement area of the container cover 16. The mark 43 provided on the surface of the intermediate floor 46 serves as an aid for the user to determine the location to which the container cover 16 has to be pulled to ensure complete exposure of the substance M stocked in the container part 14. The windowlike cutout 51 of the support section 15 initially covered by the container cover 60 is exposed while rolling off the container cover 16, with the mark 43 thereafter becoming visible through this cutout 51. Accordingly, the user is given an orientation for properly using the dispenser 1.

After the container cover has been pulled off of the container part 14, the substance M is exposed in the flow path. Due to the missing cover, the container part 14 is now part of the flow path, and correspondingly connected in terms of flow at one end to the air flow channel 27 leading to the unification section 32 and further to the air channel 12, and at the other end to the arced path channel-like section of the air flow channel 27, which at the end in turn empties into the unification section 32.

The dispenser 1 becomes flute-like for inhalation, preferably held with the thumb and index finger. Sucking on the mouthpiece 3 causes air to go through the inlet slits 29 and enter into the arced path channel 53 of the air flow channel 27, after which the entering air splits to pass through the direct channel section 31 leading directly to the unification section 32 and to pass through the container channel section 30 leading directly to the container part 14. The powdery substance M stocked in the container part 14 is carried out via this container channel section 30, after which the mass-offset air portion b in the unification section 32 combines with the air portion a via the direct channel section 31. Due to the cross sectional shape of the direct channel section 31 that tapers toward the unification section 32, a suction effect is also achieved on the section of the air flow channel 27 that likewise empties into the unification section 32, which supports the evacuation of the container part 14 via the blowing air introduced by way of the container channel section 30. During passage through the spiral, two-floor vortex chamber 7, the substance M is uniformly distributed in the air flow. Additional outside air c is mixed in via the outside air opening 41 prior to exit from the vortex chamber 7 into the suction channel 4 of the mouthpiece 3. The outside air c that is here aspirated as secondary air passes through the outside air channel 42 into the vortex chamber 7, wherein the outside air opening 41 that empties into the lower floor 38 is directed toward the opposite opening to the suction channel 4. In the bottom floor 33 of the vortex chamber 7, the outside air flow c combines with the substance-imbued air flow a, b immediately before transition into the suction channel 4.

The roof-like elongation 60 of the lid 19 (see here also the sectional view on FIG. 6) puts the outside air inlet openings 57 through which the outside air c is aspirated in a protected position, so that they cannot be inadvertently covered during a conventional inhalation process, for example by a finger.

During the inhalation process, the free container cover fan closes at least most of the removal opening 25, which preferably counteracts an aspiration of secondary air.

As a result of the described configuration, aspiration or air guidance within the housing 2 takes place while circumventing the container cover 16 displaced into the removal position for inhalation. The suction air flow that takes the substance M out of the container part 14 is guided without irritation. The arced path channel-like guidance of the air flow channel 27, further in particular also the nozzle-like tapering of the direct channel section 31 in the direction toward the unification section 32, optimizes the guidance of air in particular of the substance-imbued air flow. The dispenser 1 is suitable for inhaling various substances M, in particular substances that differ in terms of grain and/or mixture.

| Reference List | |
|---|---|
| 1 | Dispenser |
| 2 | Housing |
| 3 | Mouthpiece |
| 4 | Suction channel |
| 5 | Suction mouth |
| 6 | Closure cap |
| 7 | Vortex chamber |
| 8 | Chamber ceiling |
| 9 | Chamber floor |
| 10 | Housing part |
| 11 | Step |
| 12 | Air channel |
| 13 | Receptacle |
| 14 | Container part |
| 15 | Support section |
| 16 | Container cover |
| 17 | Puller handle |
| 18 | Blister |
| 19 | Lid |
| 20 | Cover |
| 21 | Side wall |
| 22 | Latching depression |
| 23 | Latching projection |
| 24 | Ceiling underside |
| 25 | Removal opening |
| 26 | Rear wall |
| 27 | Air flow channel |
| 28 | Deflection section |
| 29 | Air inlet slit |
| 30 | Container channel section |
| 31 | Direct channel section |
| 32 | Unification section |
| 33 | Floor |
| 34 | Annular wall |
| 35 | Annular channel |
| 36 | Floor bottom |
| 37 | Through hole |
| 38 | Floor |

12

-continued

| Reference List | |
|---|---|
| 39 | Annular channel |
| 40 | Separating wall |
| 41 | Outside air opening |
| 42 | Outside air channel |
| 43 | Mark |
| 44 | Intermediate space |
| 45 | Secondary air channel |
| 46 | Intermediate floor |
| 47 | Vertical web |
| 48 | — |
| 49 | Vertical web |
| 50 | Latching nose |
| 51 | Cutout |
| 52 | Curvature area |
| 53 | Arced path channel |
| 54 | Tapered section |
| 55 | Rib |
| 56 | Hollow surface |
| 57 | Outside air inlet opening |
| 58 | Recess |
| 59 | Projecting formation |
| 60 | Elongation |
| 61 | Edge surface |
| 62 | Front edge surface |
| 63 | Lid section |
| 64 | Side edge surface |
| 65 | Side edge surface |
| 66 | Intersection |
| 67 | Intersection |
| a | Air flow |
| b | Air flow |
| c | Air flow |
| d | Length |
| d' | Length |
| e | Width |
| f | Width |
| g | Offset dimension |
| h | Auxiliary line |
| j | Auxiliary line |
| k | Auxiliary line |
| m | Radius |
| n | Radius |
| p | Extent |
| q | Length |
| r | Removal direction |
| x | Pivoting axis |
| y | Vortex chamber axis |
| z | Longitudinal central axis |
| L | Longitudinal extension |
| M | Substance |
| U | Undergrip protrusion |

The invention claimed is:

1. A dispenser (1) for powdery substances (M) contained in a separate package, wherein the package has a container part (14) with a removable container cover (16), wherein the dispenser is configured such that an aspirated air flow is sucked predominantly through the container part (14) after removal of the container cover (16) from the container part (14), the dispenser comprising a housing part (10) and a lid (19) covering the housing part and which is pivotable around a pivoting axis (x), wherein the dispenser (1) comprises slits (29) in the lid (19) that allow air flow to enter through the lid (19), wherein the dispenser comprises an internal channel that is configured such that, in use, the air flow entering through the lid is directed into first and second air flows (a, b), wherein an air portion for accommodating the first air flow is configured to bypass the package and a mass offset air portion for accommodating the second air flow is configured to allow flow through the package, wherein a unification section (32) is provided to rejoin the air portion with the mass offset air portion such that the air flows (a, b) merge, wherein a vortex chamber (7) upstream from a mouthpiece (3), is provided and configured to receive the merged flows, wherein outside air inlet openings (57) for a third air flow (c) and a removal opening (25) for removal of the removable container cover (16) are formed in the housing part (10) covered by the lid (19), wherein, in a lid section allocated to the outside air inlet openings (57) for the third air flow (c), the lid (19) is formed with a radial elongation (60) relative to the pivoting axis (x), wherein the elongation (60) simultaneously forms an undergrip protrusion (U) for opening the lid (19) and freely extends lengthwise beyond an adjacent, unelongated lid section (63), and a length (p) of the elongation (60) in relation to the unelongated lid section (63) corresponds to one fifth or more of the width (e) of the lid (19), wherein the radial elongation (60) is formed relative to the pivoting axis (x) over a width (f) corresponding to 0.35 to 0.4 times the width (e) of the lid (19), the width (f) measured at an auxiliary line (k) that runs parallel to the pivoting axis (x), and which runs with a longitudinally offset dimension (g) to a front edge surface (62) of the radial elongation (60), in a top view of the dispenser, with the offset dimension (g) corresponding to about 0.1 times the width (e) of the lid, wherein the radial elongation (60) overhangs all of the outside air inlet openings (57) provided in the housing part (10) in a closed lid position but does not overhang the removal opening (25), wherein an outer side edge surface (65) of the elongation (60) runs continuously into a facing outer wall surface of the lid (19), wherein a marginal edge formed by the outer side edge surface (65) and the facing outer wall surface of the lid (19), in a top view of the lid (19), runs along a circular arc with a radius (m), wherein the front edge surface (62) curves toward the mouthpiece (3) in the top view and joins the outer side edge surface (65) of the marginal edge, wherein the lid (19) and the elongation (60), in a sectional view, define an upperwall surface that has a circular line with a radius (n), and wherein the radius (n) corresponds to 4 to 6 times of the width (e) of the lid (19).

2. The dispenser according to claim 1, wherein the elongation (60) is formed as a single piece and/or integrally with the lid (19).

3. The dispenser according to claim 1, wherein the unelongated lid section (63) formed adjacent to the radial elongation (60) has an edge surface (61) that extends over a rear wall (26), with a length dimension (d'), which corresponds to 0.2 to 0.5 times a length dimension (d), with which the radial elongation (60) protrudes over the rear wall (26), with the length dimension (d) corresponding to 0.25 to 0.4 times a lid length (q) removed from the pivoting axis (x) up to the front edge surface (62) of the radial elongation (60).

* * * * *